(12) United States Patent
Graham et al.

(10) Patent No.: US 10,342,665 B2
(45) Date of Patent: Jul. 9, 2019

(54) ELBOW PROSTHESIS

(71) Applicant: Encore Medical, L.P., Austin, TX (US)

(72) Inventors: Thomas J. Graham, Cockeysville, MD (US); Nicholas J. Katrana, Fort Wayne, IN (US)

(73) Assignee: Encore Medical, L.P., Austin, TX (US)

( * ) Notice: Subject to any disclaimer, the term of this patent is extended or adjusted under 35 U.S.C. 154(b) by 161 days.

(21) Appl. No.: 15/424,383

(22) Filed: Feb. 3, 2017

(65) Prior Publication Data

US 2017/0239057 A1    Aug. 24, 2017

Related U.S. Application Data

(60) Division of application No. 12/562,616, filed on Sep. 18, 2009, now Pat. No. 9,561,110, which is a (Continued)

(51) Int. Cl.
*A61F 2/38* (2006.01)
*A61F 2/30* (2006.01)

(52) U.S. Cl.
CPC .............. *A61F 2/38* (2013.01); *A61F 2/3804* (2013.01); *A61F 2/30767* (2013.01); (Continued)

(58) Field of Classification Search
CPC ............ A61F 2/3804; A61F 2002/3809; A61F 2002/3813; A61F 2002/3818; A61F 2002/3831; A61F 2002/3827
See application file for complete search history.

(56) References Cited

U.S. PATENT DOCUMENTS 3,547,115 A    12/1970   Stevens
3,694,821 A    10/1972   Moritz
(Continued)

FOREIGN PATENT DOCUMENTS

DE    2806717    2/1978
DE    3417923    11/1985
(Continued)

OTHER PUBLICATIONS

Biomet Orthopedics, Inc., 1995, AGC Total Knee System (product brochure) 11 pp.
(Continued)

*Primary Examiner* — Suba Ganesan
(74) *Attorney, Agent, or Firm* — Knobbe Martens Olson & Bear LLP

(57) ABSTRACT

An elbow prosthesis constructed in accordance to one example of the present teachings can include a capitellar implant having an articulating head and a stem. The articulating head can have a first articulating surface positioned generally between a lateral side and a medial side. A passage can extend through the articulating head from the lateral side to the medial side. The articulating head can define a counterbore formed at the lateral side and that is concentric with the passage. According to other features, the elbow prosthesis can include a coronoid implant that has a body and a stem. The body can have a superior articulating surface that includes a central ridge and an anterior buttress. The central ridge can be configured to accommodate articulation with a trochlea in an implanted position.

13 Claims, 17 Drawing Sheets

Related U.S. Application Data continuation-in-part of application No. 12/391,904, filed on Feb. 24, 2009, now Pat. No. 10,231,839, which is a continuation-in-part of application No. 11/384,943, filed on Mar. 17, 2006, now Pat. No. 8,585,768, which is a continuation-in-part of application No. 10/333,140, filed as application No. PCT/US01/22338 on Jul. 17, 2001, now Pat. No. 7,247,170.

(60) Provisional application No. 61/098,478, filed on Sep. 19, 2008, provisional application No. 60/219,103, filed on Jul. 18, 2000.

(52) U.S. Cl.
CPC ............... *A61F 2002/30507* (2013.01); *A61F 2002/30594* (2013.01); *A61F 2002/30616* (2013.01); *A61F 2002/3809* (2013.01); *A61F 2002/3813* (2013.01); *A61F 2002/3831* (2013.01); *A61F 2220/0025* (2013.01)

(56) References Cited

U.S. PATENT DOCUMENTS

| | | |
|---|---|---|
| 3,708,805 A | 1/1973 | Scales et al. |
| 3,816,854 A | 6/1974 | Schlein |
| 3,824,630 A | 7/1974 | Johnston |
| 3,852,831 A | 12/1974 | Dee |
| 3,919,725 A | 11/1975 | Swanson et al. |
| 3,939,496 A | 2/1976 | Ling et al. |
| 3,946,445 A | 3/1976 | Bentley et al. |
| 3,990,117 A | 11/1976 | Pritchard et al. |
| 3,991,425 A | 11/1976 | Martin et al. |
| 4,001,603 A | 1/1977 | Wilcox |
| 4,008,495 A | 2/1977 | Cavendish et al. |
| 4,038,704 A | 8/1977 | Ring |
| 4,079,469 A | 3/1978 | Wadsworth |
| 4,129,902 A | 12/1978 | Harmon |
| 4,131,956 A | 1/1979 | Treace |
| 4,131,957 A | 1/1979 | Bokros |
| 4,194,250 A | 3/1980 | Walker |
| 4,206,516 A | 6/1980 | Pilliar |
| 4,224,695 A | 9/1980 | Grundei et al. |
| 4,224,697 A | 9/1980 | Murray et al. |
| 4,242,758 A | 1/1981 | Amis et al. |
| 4,259,752 A | 4/1981 | Taleisnik |
| 4,280,231 A | 7/1981 | Swanson |
| 4,293,963 A | 10/1981 | Gold et al. |
| 4,301,552 A | 11/1981 | London |
| 4,352,212 A | 10/1982 | Greene et al. |
| 4,378,607 A | 4/1983 | Wadsworth |
| 4,383,337 A | 5/1983 | Volz et al. |
| 4,479,271 A | 10/1984 | Bolesky et al. |
| 4,538,306 A | 9/1985 | Dorre et al. |
| 4,659,331 A | 4/1987 | Matthews et al. |
| 4,725,280 A | 2/1988 | Laure |
| 4,759,768 A | 7/1988 | Hermann et al. |
| 4,790,854 A | 12/1988 | Harder et al. |
| 4,822,364 A | 4/1989 | Inglis et al. |
| 4,911,719 A | 3/1990 | Merle |
| 4,927,422 A | 5/1990 | Engelhardt |
| 4,936,853 A | 6/1990 | Fabian et al. |
| 5,024,670 A | 6/1991 | Smith et al. |
| 5,030,237 A | 7/1991 | Sorbie et al. |
| 5,207,711 A | 5/1993 | Caspari et al. |
| 5,282,367 A | 2/1994 | Moore et al. |
| 5,282,867 A | 2/1994 | Mikhail |
| 5,285,367 A | 2/1994 | Moore et al. |
| 5,314,484 A | 5/1994 | Huene |
| 5,376,121 A | 12/1994 | Huene et al. |
| 5,380,334 A | 1/1995 | Torrie et al. |
| 5,411,555 A | 5/1995 | Nieder |
| 5,458,644 A | 10/1995 | Grundel |
| 5,507,821 A | 4/1996 | Sennwald et al. |
| 5,507,826 A | 4/1996 | Besselink et al. |
| 5,549,685 A | 8/1996 | Hayes |
| 5,584,835 A | 12/1996 | Greenfield |
| 5,665,087 A | 9/1997 | Huebner |
| 5,702,471 A | 12/1997 | Grundei et al. |
| 5,725,541 A | 3/1998 | Anspach et al. |
| 5,725,591 A | 3/1998 | DeCarlo, Jr. et al. |
| 5,782,923 A | 7/1998 | Engelbrecht et al. |
| 5,840,078 A | 11/1998 | Yerys |
| 5,879,395 A | 3/1999 | Tornier et al. |
| 5,928,285 A | 7/1999 | Bigliani et al. |
| 5,980,557 A | 11/1999 | Iserin et al. |
| 6,027,534 A | 2/2000 | Wack et al. |
| 6,120,543 A | 9/2000 | Kubein-Meesenburg et al. |
| 6,162,253 A | 12/2000 | Conzemius et al. |
| 6,290,725 B1 | 9/2001 | Weiss et al. |
| 6,306,171 B1 | 10/2001 | Conzemius |
| 6,379,387 B1 | 4/2002 | Tornier |
| 6,500,208 B1 | 12/2002 | Metzger et al. |
| 6,626,906 B1 | 9/2003 | Young |
| 6,656,225 B2 | 12/2003 | Martin |
| RE38,409 E | 1/2004 | Noiles |
| 6,699,290 B1 | 3/2004 | Wack et al. |
| 6,716,248 B2 | 4/2004 | Huene |
| 6,767,368 B2 | 7/2004 | Tornier et al. |
| 6,814,757 B2 | 11/2004 | Kopylov et al. |
| 6,890,357 B2 | 5/2005 | Tornier |
| 7,247,170 B2 | 7/2007 | Graham et al. |
| 7,527,650 B2 | 5/2009 | Johnson et al. |
| 7,604,666 B2 | 10/2009 | Berelsman et al. |
| 7,625,406 B2 | 12/2009 | Berelsman et al. |
| 8,585,768 B2 | 11/2013 | Berelsman et al. |
| 8,932,362 B2 | 1/2015 | Katrana et al. |
| 8,998,995 B2 | 4/2015 | Katrana et al. |
| 9,034,050 B2 | 5/2015 | Katrana et al. |
| 9,561,110 B2 | 2/2017 | Graham et al. |
| 2002/0055783 A1 | 5/2002 | Tallarida et al. |
| 2002/0165614 A1 | 11/2002 | Tornier |
| 2004/0186580 A1 | 9/2004 | Steinmann |
| 2004/0243243 A1 | 12/2004 | Tornier |
| 2004/0254574 A1 | 12/2004 | Morrison et al. |
| 2005/0049710 A1* | 3/2005 | O'Driscoll ............ A61F 2/3804 623/20.11 |
| 2005/0216090 A1 | 9/2005 | O'Driscoll et al. |
| 2006/0224243 A1 | 10/2006 | Pare |
| 2006/0247786 A1 | 11/2006 | Ball |
| 2008/0154384 A1 | 6/2008 | Acker et al. |
| 2008/0183291 A1 | 7/2008 | Scheller et al. |
| 2008/0188942 A1 | 8/2008 | Brown et al. |
| 2009/0105839 A1 | 4/2009 | Ikegami et al. |
| 2010/0179661 A1 | 7/2010 | Berelsman et al. |
| 2010/0305710 A1 | 12/2010 | Wagner et al. |
| 2012/0136450 A1 | 5/2012 | Wendelburg et al. |
| 2013/0345818 A1 | 12/2013 | Wagner et al. |
| 2014/0324175 A1 | 10/2014 | Katrana et al. |
| 2015/0250600 A1 | 9/2015 | Katrana et al. |
| 2015/0289982 A1 | 10/2015 | Katrana et al. |
| 2017/0367832 A1 | 12/2017 | Katrana et al. |

FOREIGN PATENT DOCUMENTS

| | | |
|---|---|---|
| DE | 3940728 | 6/1991 |
| EP | 1 051 954 | 11/2000 |
| EP | 1 481 653 | 12/2004 |
| FR | 2419718 | 10/1979 |
| FR | 2634373 | 1/1990 |
| GB | 1 520 162 | 8/1978 |
| SU | 1560-183 | 4/1990 |
| SU | 1567-200 | 5/1990 |
| WO | WO 00/23012 | 4/2000 |
| WO | WO 13/006536 | 1/2013 |

OTHER PUBLICATIONS

DePuy Orthopaedics, Inc., 2000, Elbow Replacement Surgery, http://www.allaboutarthritis.com/AllAboutArthritis/layoutTemplates/h-tml/en/contentdisplay/document/condition/arthritis/clinicalArticle/

(56) References Cited

OTHER PUBLICATIONS

Elbow.s- ub.--Replacement.sub.--Surgery.htm, 3 pp.
Biomet Orthopedics, Inc., 2002, Discovery Elbow System Surgical Technique (product brochure), 20 pp.
DePuy Orthopaedics, Inc., 2000, Acclaim Total Elbow Replacement System: Overview, www.jointreplacement.com/xq/ASP.default/mn.local/pg.list/joint_id.2/list_id.59/newFont.2/joint_nm.Elbow/local_id.18/qx/default.htm, 3 pp.
DePuy Orthopaedics, Inc., 2000, Acclaim Total Elbow Replacement System: Surgery, www.jointreplacement.com/xq/ASP.default/mn.local/pg.list/joint_id.2-/list_id.59/newFont.2/joint_nm.Elbow/local_id.18/qx/default.htm, 3 pp.
Tornier, Latitude®, Total Elbow Prosthesis: A New Generation is Born Naturally Precise (product brochure), 4 pp. undated.
Tornier, Latitude® Total Elbow Prosthesis: Surgical Technique (product brochure), 40 pp., undated.
Wright Medical Technology, Inc., 2003, Extremities: Sorbie-Questor® Total Elbow System (product brochure), 1 p.
International Search Report for PCT/US01/22338 dated Jan. 3, 2002.
Non-final Office Action dated Apr. 13, 2010 in U.S. Appl. No. 11/384,943.
Final Office Action dated Oct. 27, 2010 in U.S. Appl. No. 11/384,943.
Non-final Office Action dated Apr. 12, 2011 in U.S. Appl. No. 11/384,943.
Final Office Action dated Dec. 12, 2011 in U.S. Appl. No. 11/384,943.
Office Action dated Nov. 1, 2012 in U.S. Appl. No. 12/391,904.
Office Action dated Mar. 27, 2015 in U.S. Appl. No. 12/391,904.
Non-Final Office Action regarding U.S. Appl. No. 12/780,424, dated Nov. 2, 2012.
Office Action dated Aug. 29, 2014 in U.S. Appl. No. 14/221,383.
Office Action dated Feb. 1, 2016 in U.S. Appl. No. 14/221,383.
Office Action dated Jun. 19, 2013 in U.S. Appl. No. 13/051,559.
Office Action dated Apr. 23, 2014 in U.S. Appl. No. 13/051,559.
Office Action dated Feb. 7, 2014 in U.S. Appl. No. 13/465,690.
Office Action dated Aug. 18, 2014 in U.S. Appl. No. 13/465,690.
International Search Report and Written Opinion for PCT/US2010/049314 dated Feb. 21, 2011.
International Search Report and Written Opinion for PCT/US2009/057449 dated Feb. 21, 2011.
International Preliminary Report on Patentability and Written Opinion for PCT/US2009/057449 dated Sep. 9, 2011.
International Search Report and Written Opinion of the International Searching Authority regarding International Application No. PCT/US2014/021970, dated May 12, 2014.
International Search Report and Written Opinion dated Nov. 8, 2012 in PCT/US12/045207.
Non-Final Office Action regarding U.S. Appl. No. 12/562,616, dated May 17, 2012.
Office Action dated Apr. 9, 2014 in U.S. Appl. No. 12/562,616.
Office Action dated Dec. 29, 2014 in U.S. Appl. No. 12/562,616.
Office Action dated Jun. 26, 2015 in U.S. Appl. No. 12/562,616.

\* cited by examiner

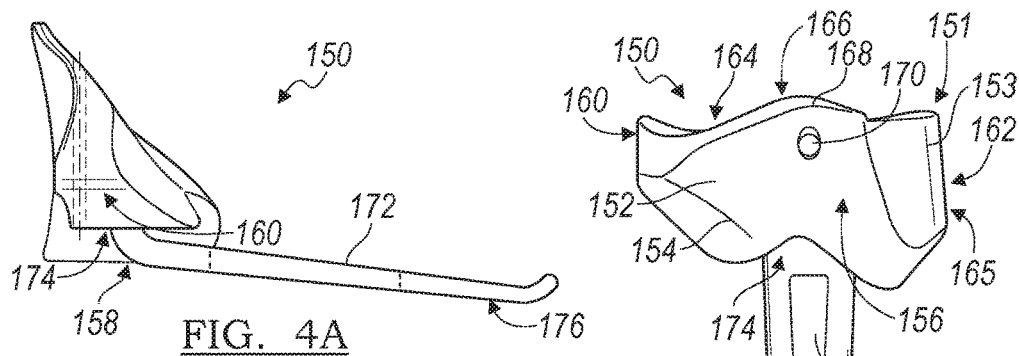
FIG. 4A
FIG. 4B
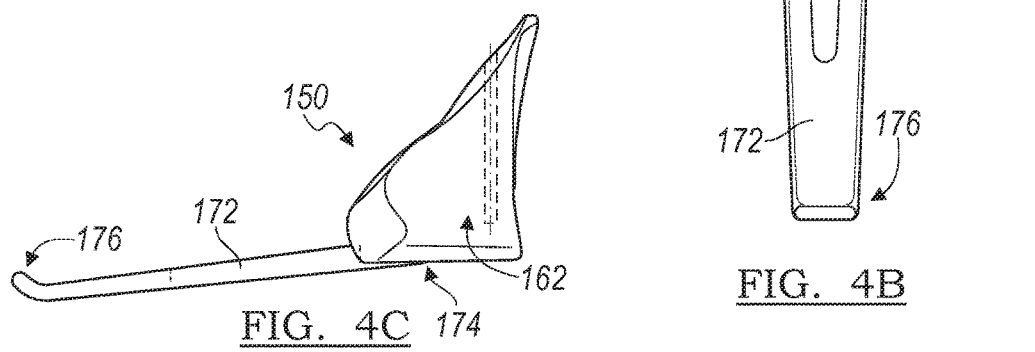
FIG. 4C
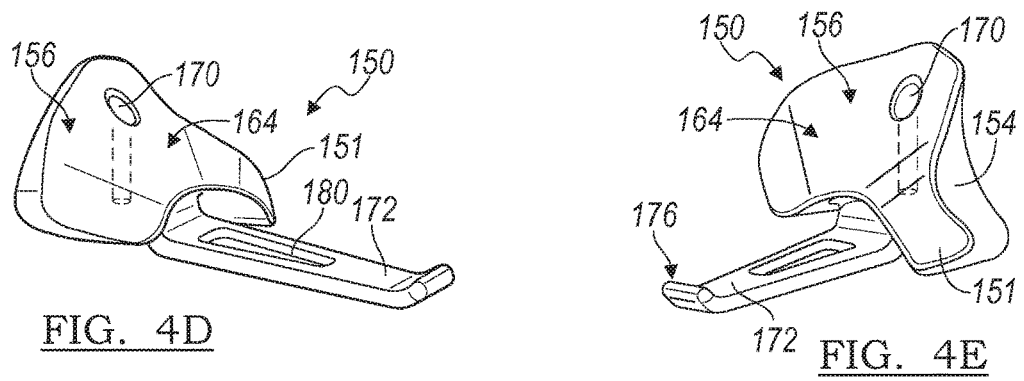
FIG. 4D
FIG. 4E
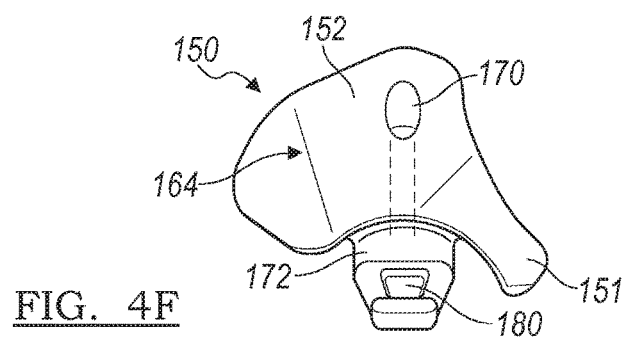
FIG. 4F

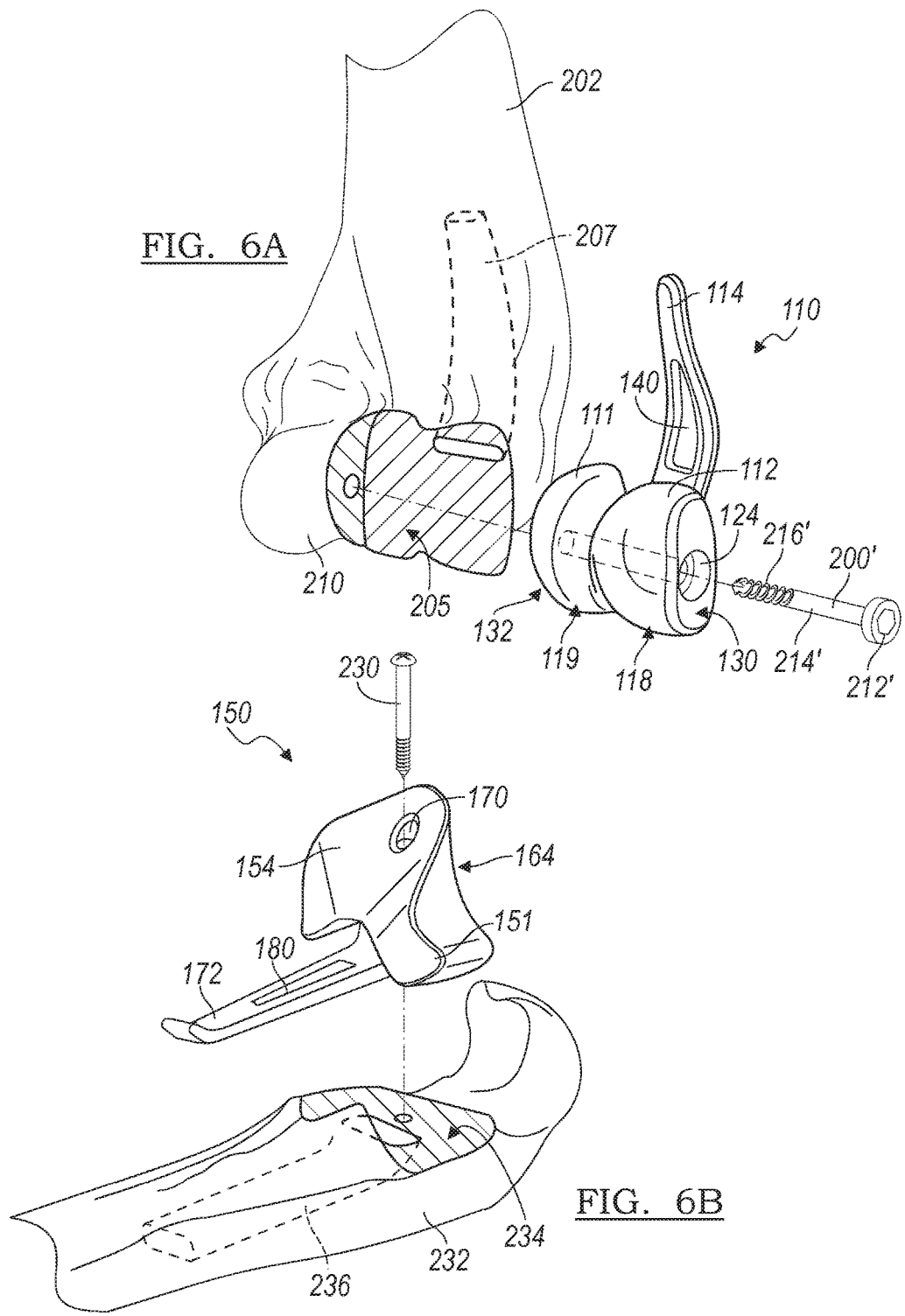

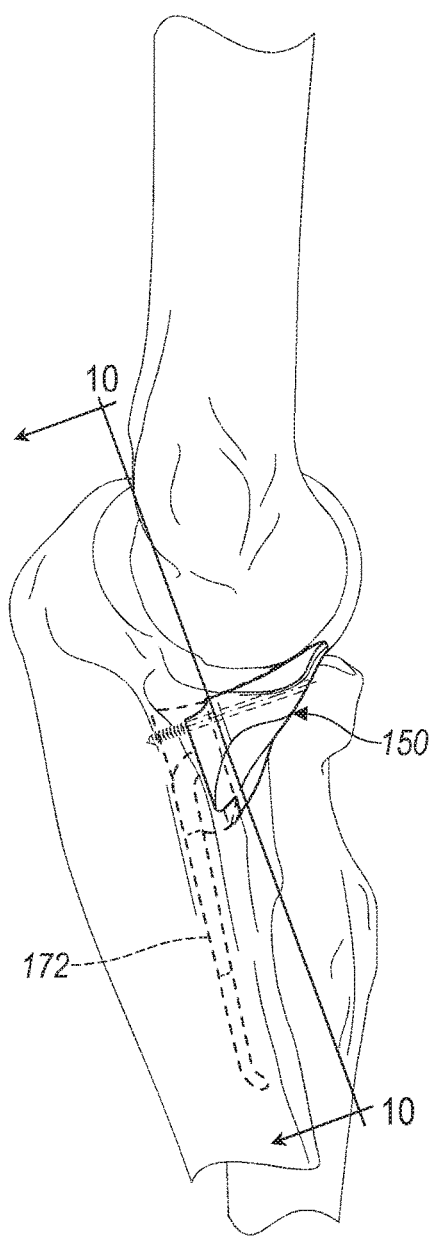 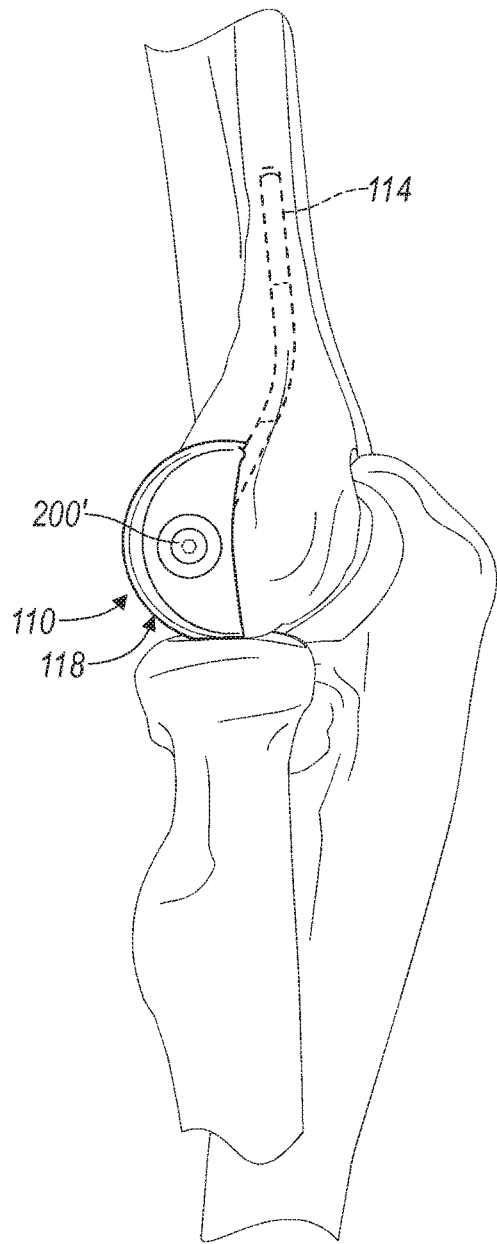
FIG. 6E
FIG. 6F

ELBOW PROSTHESIS

CROSS-REFERENCE TO RELATED APPLICATIONS

Any and all applications for which a foreign or domestic priority claim is identified in the Application Data Sheet as filed with the present application are hereby incorporated by reference under 37 CFR 1.57. This application is a divisional of U.S. patent application Ser. No. 12/562,616, filed Sep. 18, 2009, which a is continuation-in-part of U.S. patent application Ser. No. 12/391,904, filed on Feb. 24, 2009, which is a continuation-in-part of U.S. patent application Ser. No. 11/384,943, filed on Mar. 17, 2006, now U.S. Pat. No. 8,585,768, which is a continuation-in-part of U.S. patent application Ser. No. 10/333,140 filed on Jan. 15, 2003, now U.S. Pat. No. 7,247,170, which is a National Stage of International Application No. PCT/US01/22338 (published as WO 02/05728), filed Jul. 17, 2001, which claims priority to U.S. Provisional Application No. 60/219,103 filed Jul. 18, 2000. Each of these applications are incorporated herein by reference.

U.S. patent application Ser. No. 11/780,365 filed on Jul. 19, 2007, now U.S. Pat. No. 7,625,406 and U.S. patent application Ser. No. 11/780,370 filed on Jul. 19, 2007, now U.S. Pat. No. 7,604,666 disclose related subject matter. These applications are also incorporated by reference.

U.S. application No. 12/562,616 also claims priority to U.S. Provisional Application No. 61/098,478, filed Sep. 19, 2008. This application is also incorporated by reference.

FIELD

The present teachings relate generally to prosthetic devices used in arthroplasty and more particularly to a modular elbow prosthesis.

BACKGROUND

The present teachings relate generally to prosthetic devices used in arthroplasty and more particularly to a modular elbow prosthesis including a capitellar implant and a coronoid implant.

In general, elbow prostheses have been provided and can generally include linked and unlinked versions. Linked or constrained elbow prostheses are known which comprise simple hinge arrangements, one component of which is attached to the end of the humerus and the other component of which is attached to the end of the ulna. The humeral component includes a shaft, that is cemented (or press-fit uncemented) into a prepared cavity in the end of the humerus, and the ulnar component includes a shaft, that is cemented (or press-fit uncemented) to the end of the ulna. The components of the prosthesis are connected together by means of a hinge pin so that the prosthesis allows a single degree of freedom of movement of the ulna relative to the humerus. Unlinked, or unconstrained, elbow prostheses are known which are similar to linked elbow prostheses but do not have a specific component which mechanically couples the humeral and ulnar stems together. Rather, the prosthetic device is held together by the patient's natural soft tissues.

In some instances, it may be desirable to replace portions of bone in an elbow, such as to address certain fractures. Some fractures, such as about the capitellum and coronoid can be the most technically challenging to reconstruct. Difficult exposure, inconsistent fracture fragment size, poor bone quality and other factors conspire to result in suboptimal outcomes such as nonunion, instability and accelerated arthritis.

SUMMARY

An elbow prosthesis constructed in accordance with one example of the present teachings can include a capitellar implant having an articulating head and a stem. The articulating head can have a first articulating surface positioned generally between a lateral side and a medial side. A passage can extend through the articulating head from the lateral side to the medial side. The articulating head can define a counterbore formed on the lateral side and concentric with the passage.

The elbow prosthesis can further comprise a bone screw having a shank and a head. The shank can have a length greater than the passage through the articulating head, such that the head nests in the counterbore and at least a portion of the shank extends proud from the medial side of the articulating head in an implanted position. The stem can define an opening therethrough. The opening can be adapted to accept bony ingrowth when implanted into an intramedullary canal of a humerus. The stem can include a connecting end and a distal end. The connecting end can be attached to the articulating head. The stem can have a curved intermediate portion that positions the distal end posteriorly relative to the connecting end in an implanted position.

The articulating head can be modular and be adapted to be selectively coupled to the stem according to further features. The stem can be intraoperatively coupled to the articulating head. The stem can include a first interlocking geometry formed at the connecting end and the articulating head can include a second interlocking geometry. The first and second interlocking geometries can mate in an assembled position. According to one example, the first interlocking geometry can include a T-shaped male insertion portion and the second interlocking geometry can include a T-shaped female receiving portion. A throughbore can be defined through the first interlocking geometry that accommodates the bone screw in an implanted position.

According to additional features, the articulating head can further comprise an extension portion that extends generally medially from the medial side of the articulating head. The extension portion can have a second articulating surface that is adapted to replace at least part of a trochlea.

According to other features, the elbow prosthesis can include a coronoid implant that has a body and a stem. The body can have a superior articulating surface that includes a central ridge and an anterior buttress. The central ridge can be configured to accommodate articulation with a trochlea in an implanted position. A passage can extend through the body from an anterior to a posterior side.

A bone screw can extend into the passage of the body. The bone screw can have a distal tip that extends proud from the body and is adapted to threadably engage a host ulna in an implanted position. In one example, the bone screw can extend generally perpendicular relative to a long axis of the stem. In other examples, variable angle lock screws can be used to obtain improved bone quality for fixation. The body can additionally comprise an extension portion that is adapted to extend generally laterally toward a radial head of a radius in an implanted position.

Further areas of applicability will become apparent from the description provided herein. It should be understood that the description and specific examples are intended for purposes of illustration only and are not intended to limit the scope of the present disclosure.

DRAWINGS

Additional advantages and features of the present teachings will become apparent from the subsequent description and the appended claims, taken in conjunction with the accompanying drawings, wherein:

FIG. 4A is a medial view of a coronoid implant constructed in accordance to another example of the present teachings;

FIG. 4B is an anterior view of the coronoid implant of FIG. 4A;

FIG. 4C is a lateral view of the coronoid implant of FIG. 4A;

FIG. 4D is a perspective medial view of the coronoid implant of FIG. 4A;

FIG. 4E is a perspective lateral view of the coronoid implant of FIG. 4A;

FIG. 4F is an inferior view of the coronoid implant of FIG. 4A;

FIG. 6A is a lateral perspective view of the capitellar implant of FIGS. 3A-3E and a bone screw shown adjacent to a prepared distal humerus where a portion of the trochlea has been resected to accommodate an extension portion of the capitellar implant;

FIG. 6B is a lateral perspective view of the coronoid implant of FIGS. 4A-4F shown with a bone screw and adjacent to a prepared ulna;

FIG. 6E is a medial view of the coronoid implant of FIGS. 4A-4F shown implanted into a host ulna of a left elbow in extension;

FIG. 6F is a lateral view of the capitellar implant of FIGS. 3A-3E shown implanted into a host humerus and with the elbow in extension;

FIG. 11B is a lateral perspective view of a left elbow and shown with the capitellar, coronoid and radial implants of FIG. 11A;

DETAILED DESCRIPTION OF VARIOUS EMBODIMENTS

Figure 1A:
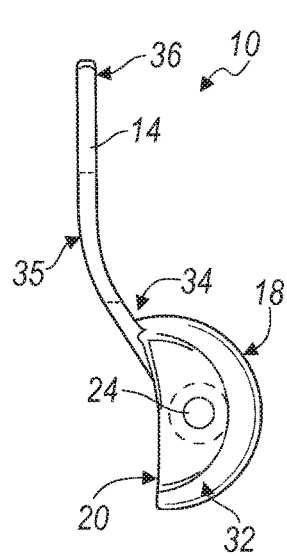
FIG. 1A is a medial view of a capitellar implant constructed in accordance to the present teachings.

The following description is merely exemplary in nature and is not intended to limit the present disclosure, application, or uses. It should be understood that throughout the drawings, corresponding reference numerals indicate like or corresponding parts and features.

At the outset, the following discussion and related figures relate to elbow prostheses including capitellar and coronoid implants constructed for implantation into a left elbow, however, it will be appreciated that the same implants can similarly be provided for a right elbow. In this way, a right capitellar and/or coronoid implant can be formed similarly but geometrically inversed in the medial/lateral direction.

Figure 1B:
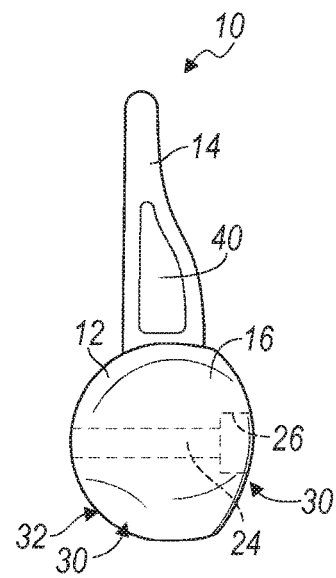
FIG. 1B is an anterior view of the capitellar implant of FIG. 1A.
Figure 1C:
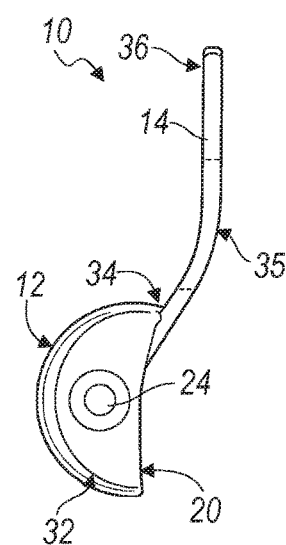
FIG. 1C is a lateral view of the capitellar implant of FIG. 1A.
Figure 1D:
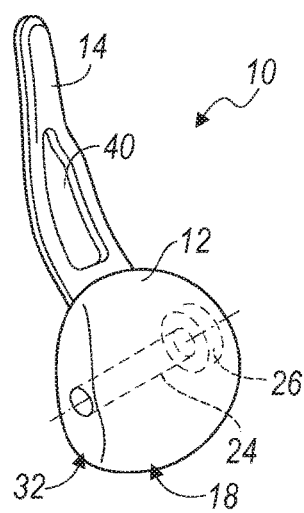
FIG. 1D is a perspective medial view of the capitellar implant of FIG. 1A.
Figure 1E:
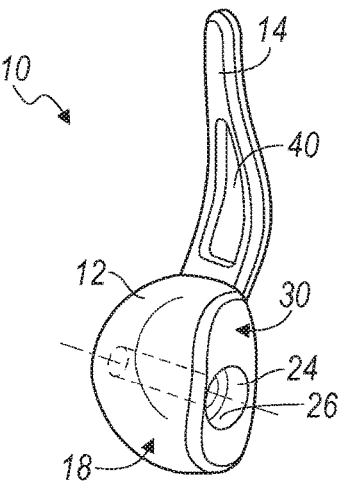
FIG. 1E is a perspective lateral view of the capitellar implant of FIG. 1A.

With initial reference to FIGS. 1A-1E, a capitellar implant 10 constructed in accordance to one example of the present teachings will be described. In general, the capitellar implant 10 can be implanted at the distal humerus (FIG. 5A) in circumstances where it is desirable to accommodate fracture patterns along the articulating surfaces or other informalities observed about the distal humeral articular surface. The capitellar implant 10 generally comprises an articulating head 12 and a stem 14. The articulating head 12 can include an articulating body 16 having an arcuate articulating surface 18 and a humeral engaging surface 20. A passage 24 having a counterbore 26 can be formed through the articulating body 16 from a lateral side 30 to a medial side 32 of the articulating body 16. As will be described, the passage 24 is operable to receive a bone screw during implantation. As best illustrated in FIGS. 1A and 1C, the articulating surface 18 is generally hemispherical around the articulating body 16. The humeral engaging surface 20 can be generally concave such that the articulating surface 18 is provided around an area greater than 180 degrees of the articulating body 16. In some examples, the concave humeral engaging surface 20 can facilitate nesting of a prepared distal humerus. The humeral engaging surface 20 can be porous coated or roughened to further encourage bony ingrowth. As best illustrated in FIG. 1B, the anterior profile of the articulating body 16 can be generally circular and has a truncated lateral side 30. The lateral side 30 can generally provide a shallower radius relative to a remainder of the articulating body 16.

The articulating body 16 can be provided on a capitellar implant 10 having a geometry that substantially replicates at least portions of a natural capitellum of the patient. In this way, a plurality of capitellar implants 10 can be provided having articulating heads 12 with various geometries such that a surgeon can select an appropriate match based upon any given patient's particular needs or fracture areas.

The stem 14 can generally extend from a connecting end 34 that is attached to the articulating body 16 through a curved intermediate portion 35 to a proximal end 36. In general, the stem 14 can have a generally planar body that shifts posteriorly from the connecting end 34 through the curved intermediate portion 35 to the proximal end 36. The planar body can promote rotational stability. The stem 14 can define an opening 40 that can facilitate bone ingrowth when implanted into a prepared canal of a humerus. The opening 40 can have a generally triangular profile. In other examples, the opening 40 can be used to receive one or more bone screws for securably positioning the stem 14 relative to a humerus. While the figures described herein are directed toward implanting the stem 14 into a prepared canal of a humerus, the capitellar implant 10 can additionally or alternatively be positioned on an anterior face of a humerus. In one example, the stem 14 and/or the articulating head 12 can be formed of bio-compatible materials such as, but not limited to, any combinations of titanium, cobalt, polyethylene, pyrocarbon, PEEK, including carbon fiber reinforced PEEK, or other materials.

Figure 2A:
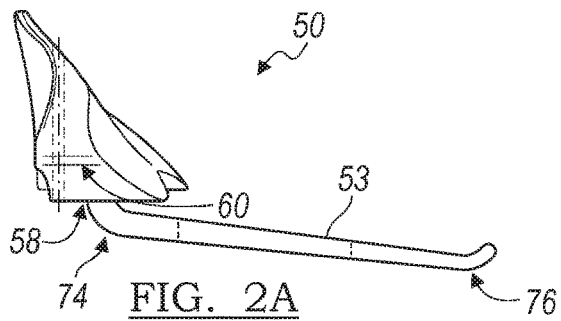
FIG. 2A is a medial view of a coronoid implant constructed in accordance to one example of the present teachings.
Figure 2B:
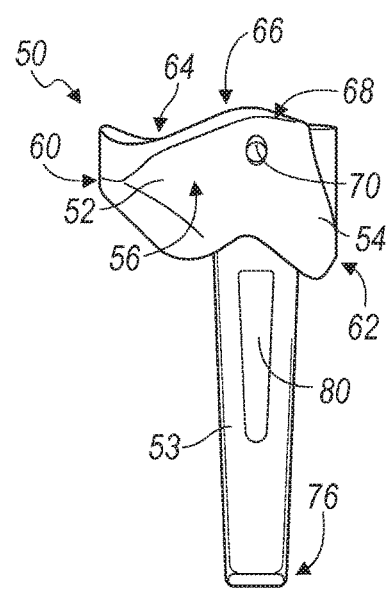
FIG. 2B is an anterior view of the coronoid implant of FIG. 2A.
Figure 2C:
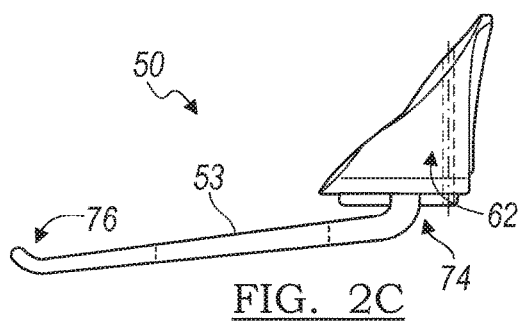
FIG. 2C is a lateral view of the coronoid implant of FIG. 2A.
Figure 2D:
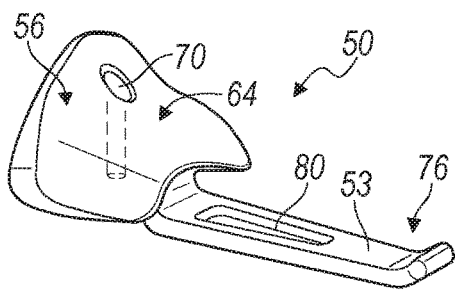
FIG. 2D is a perspective medial view of the coronoid implant of FIG. 2A.
Figure 2E:
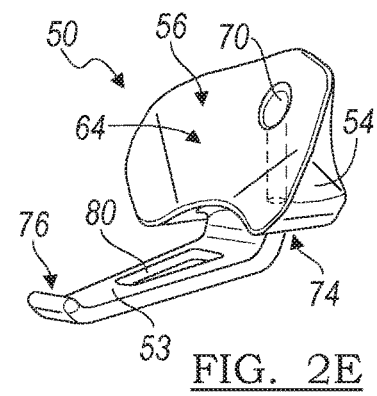
FIG. 2E is a perspective lateral view of the coronoid implant of FIG. 2A.
Figure 2F:
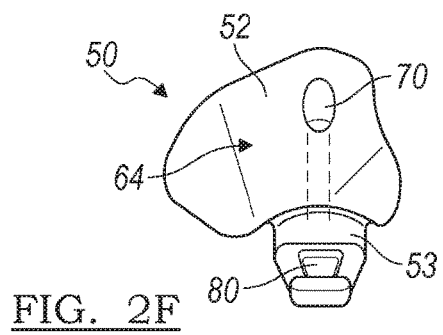
FIG. 2F is an inferior view of the coronoid implant of FIG. 2A.
Figure 3A:
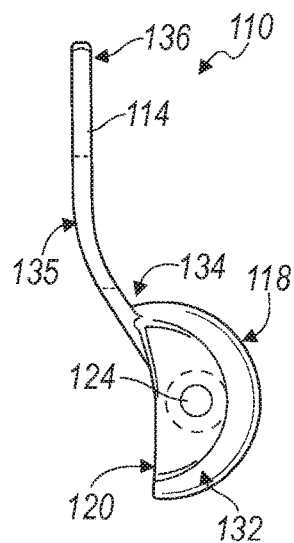
FIG. 3A is a medial view of a capitellar implant constructed in accordance to other features of the present teachings.
Figure 3B:
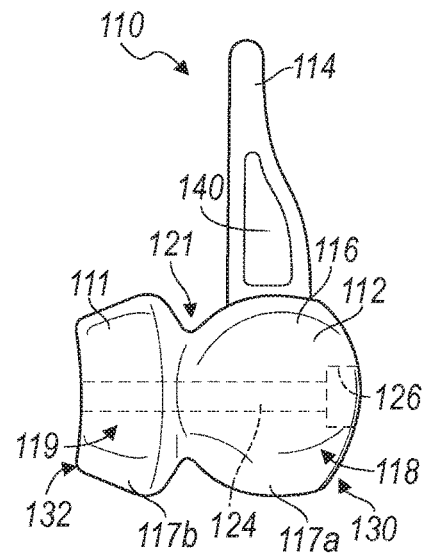
FIG. 3B is an anterior view of the capitellar implant of FIG. 3A.
Figure 3C:
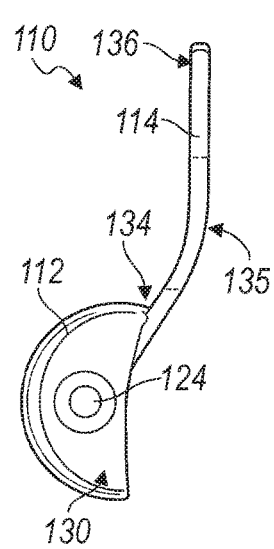
FIG. 3C is a lateral view of the capitellar implant of FIG. 3A.
Figure 3D:
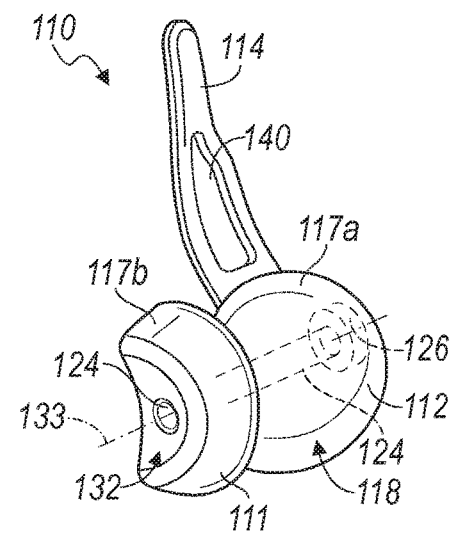
FIG. 3D is a perspective medial view of the capitellar implant of FIG. 3A.
Figure 3E:
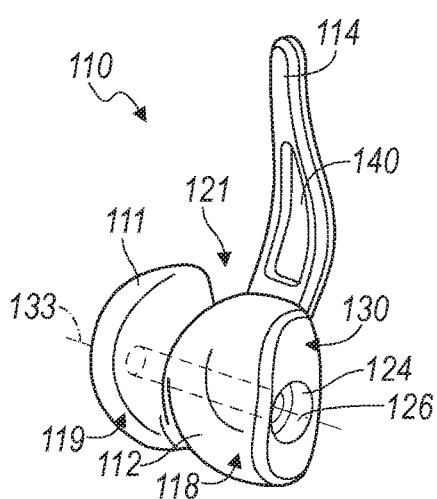
FIG. 3E is a perspective lateral view of the capitellar implant of FIG. 3A.

With reference now to FIGS. 2A-2F, a coronoid implant 50 constructed in accordance with one example of the present teachings will be described. Again, the coronoid implant 50 is constructed for use with a left elbow. However, a similar coronoid implant can be provided for a right elbow having a similar geometry that is inversed in the medial/lateral direction. In general, the coronoid implant 50 can be implanted relative to a host ulna (FIG. 5B) to replace at least portions of a host coronoid that may have experienced a fracture or other defect. The coronoid implant 50 can generally comprise an articulating portion 52 and a stem 53. The articulating portion 52 can have a body 54 having a generally triangular wedge-like shape that extends between an anterior side 56 (FIG. 2A), a posterior side 58 (FIG. 2B), a medial side 60 (FIG. 2A), and a lateral side 62 (FIG. 2C). The body 54 can include a superior articulating surface 64, a central ridge 66 and an anterior buttress 68. In one example, the posterior side 58 has a non-planar profile that is operable to engage a prepared bone surface of an ulna. The non-planar profile can facilitate rotational stability. The central ridge 66 extends in the anterior/posterior direction. The anterior buttress 68 extends generally in the medial/lateral direction and is substantially transverse to the central ridge 66. A passage 70 is formed through the body 54 from the anterior side 56 to the posterior side 58. As will be described, the passage 70 is operable to receive a bone screw during implantation of the coronoid implant 50. The stem 53 can having a planar body that extends generally from a connecting end 74 to a distal end 76. The planar body of the stem 53 can promote rotational stability. In one example, the distal end 76 can be curved at a terminal tip in a generally anterior direction relative to a long axis of the stem 53. The stem 53 can define an opening 80. The opening 80 can facilitate boney ingrowth when implanted relative to an ulna. In other examples, the opening 80 can be adapted to receive one or more bone screws to further supplement fixation of the coronoid implant 50 relative to a host ulna.

Turning now to FIGS. 3A-3E, a capitellar implant 110 constructed in accordance with another example of the present teachings will be described. In general, the capitellar implant 110 can be formed similar to capitellar implant 10 as described above with respect to FIGS. 1A-1E, but additionally includes an extension portion 111. The capitellar implant 110 can be used in circumstances where it may be desirable to replace the lateral trochlear, or portions thereof, in instances where a more extensive coronal shear pattern or other defect may be observed in the host capitellum.

The capitellar implant 110 generally comprises an articulating head 112 and a stem 114. The articulating head 112 can include an articulating body 116 having a pair of bulbous portions 117a and 117b that have a first arcuate articulating surface 118 and a second arcuate articulating surface 119, respectively. The articulating body 116 can also include a humeral engaging surface 120. The bulbous portions 117a and 117b can be laterally offset by a narrowed region 121. The second arcuate articulating surface 119 can be provided on the extension portion 111. A passage 124 having a counterbore 126 can be formed through the articulating body 116 from a lateral side 130 to a medial side 132 of the articulating body 116. As will be described, the passage 124 is operable to receive a bone screw during implantation of the capitellar implant 110. The respective first and second articulating surfaces 118 and 119 can be centered about a common axis 133. The axis 133 can be coaxial with the passage 124. The articulating body 116 can be provided on a capitellar implant 110 having a geometry that substantially replicates at least portions of a natural capitellum and trochlea of a patient. In this way, a plurality of capitellar implants 110 can be provided having articulating heads 112 with various geometries such that a surgeon can select an appropriate match based upon any given patient's particular needs. The stem 114 can generally extend from a connecting end 134 that is attached to the articulating body 116 through a curved intermediate portion 135 to a proximal end 136. In general, the stem 114 shifts posteriorly from the connecting end 134 through the curved intermediate portion 135 to the proximal end 136. The stem 114 can define an opening 140 that can facilitate bone ingrowth when implanted into a prepared canal of a humerus. In other examples, the opening 140 can be used to receive one or more bone screws for securably positioning the stem 114 relative to a humerus. The capitellar implant 110 can additionally or alternatively be positioned such that the stem 114 is positioned on an anterior face of the humerus. In one example, the stem 114 and/or the articulating head 112 can be formed of biocompatible materials such as, but not limited to, any combinations or titanium, cobalt, polyethylene, pyrocarbon, PEEK, including carbon fiber reinforced PEEK, or other materials.

With reference now to FIGS. 4A-4F, a coronoid implant 150 constructed in accordance with one example of the present teachings will be described. In general, the coronoid implant 150 can be implanted relative to a host ulna to replace at least portions of a host coronoid that may have experienced a fracture or other defect. The coronoid implant 150 is constructed similar to the coronoid implant 50 as described above with respect to FIGS. 2A-2F and further includes a lateral extension portion 151. The lateral extension portion 151 can be particularly useful in instances where it is desirable to accommodate varying amounts of the lesser sigmoid fossa, which articulates with the radial head.

The coronoid implant 150 can generally comprise a first articulating portion 152 and a second articulating portion 153. The first and second articulating portions 152 and 153 can be formed on a generally triangular wedge-shaped body 154 that extends between an anterior side 156 (FIG. 4B), a posterior side 158 (FIG. 4A), a medial side 160 (FIG. 4A), and a lateral side 162 (FIG. 4C). The body 154 can include a superior articulating surface 164 provided on the first articulating portion 152 and a radial articulating surface 165 provided on the second articulating portion 153. The body 154 can further include a central ridge 166 and an anterior buttress 168. In one example, the posterior side 158 has a non-planar profile that is operable to engage a prepared bone surface of an ulna. The non-planar profile can facilitate rotational stability. The central ridge 166 extends in the anterior/posterior direction. The anterior buttress 168 extends generally in the medial/lateral direction and is substantially transverse to the central ridge 166. A passage 170 is formed through the body 154 from the anterior side 156 to the posterior side 158. As will be described, the passage 170 is operable to receive a bone screw during implantation of the coronoid implant 150. A stem 172 can have a planar body that extends generally from a connecting end 174 to a distal end 176. In one example, the distal end 176 can be curved at a terminal tip in a generally anterior direction relative to a long axis of the stem 172. The stem 172 can define an opening 180. The opening 180 can facilitate boney ingrowth when implanted relative to an ulna. In other examples, the opening 180 can be adapted to receive one or more bone screws to further supplement fixation of the coronoid implant 150 relative to a host ulna.

Figure 5A:
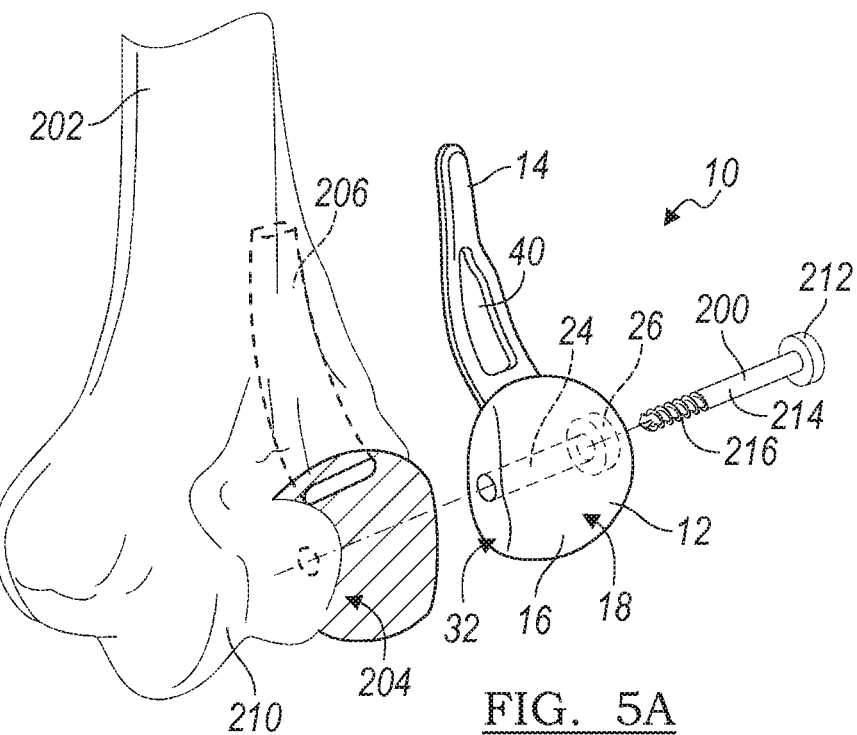
FIG. 5A is an exploded medial perspective view of the capitellar implant of FIGS. 1A-1E and a bone screw shown prior to implantation onto a prepared distal left humerus.

With reference now to FIG. 5A, the capitellar implant 10 is shown with a bone screw 200 adjacent to a humerus 202. An implant engaging surface 204 can be prepared on the distal humerus subsequent to resecting at least portions of a capitellum. In some examples, the implant engaging surface 204 can be milled or cut in a non-planar shape that corresponds to the humeral engaging surface 20. A passage 206 can be prepared that can correspond with alignment to an intramedullary canal of the humerus 202. It is appreciated that the surface 204 and the passage 206 may take other forms than that shown in the example of FIG. 5A. However, it will be appreciated that the capitellar implant 10 can be implanted onto a distal humerus to accommodate coronal shear fractures involving the lateral aspect of a trochlea 210. The bone screw 200 can include a head 212 and a shank 214 having a threaded end 216. As will become appreciated, the axial length of the bone screw 200 is greater than the width of the body 16 from the lateral side 30 to the medial side 32 of the articulating head 12, such that at least portions of the threaded end 216 can extend proud from the medial side 32 of the articulating head 12. In one example, the head 212 can provide a geometry substantially complementary to the counterbore 26 provided in the body 16.

Figure 5B:
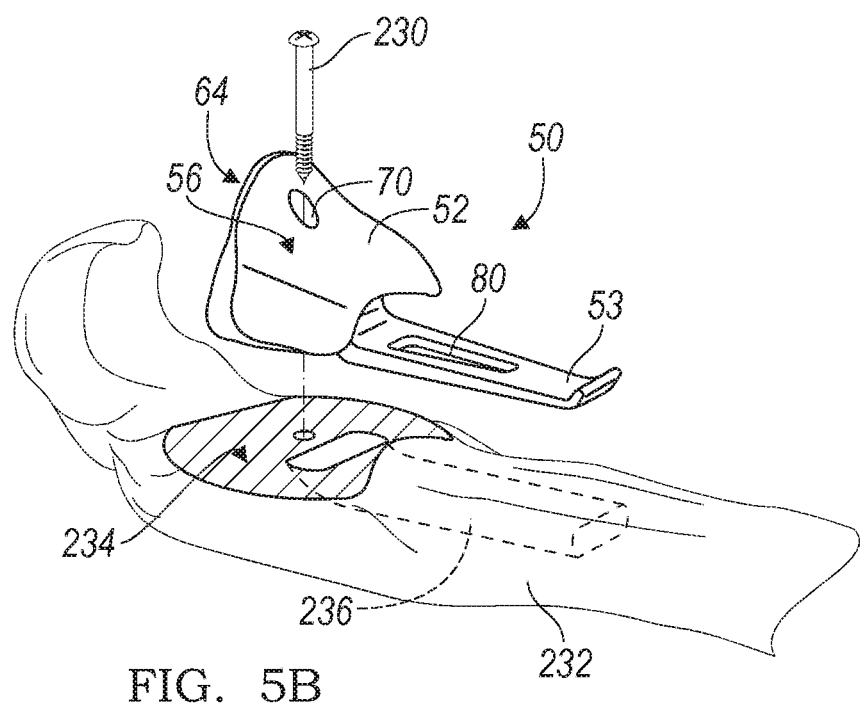
FIG. 5B is an exploded medial perspective view of the coronoid implant of FIGS. 2A-2F and a bone screw shown adjacent to a prepared proximal left ulna.

Turning now to FIG. 5B, the coronoid implant 50 is shown in exploded view with a bone screw 230 and adjacent to an ulna 232. In the example shown in FIG. 5B, the ulna 232 includes an implant engaging surface 234 where a host coronoid has been resected from the ulna 232. In some examples, the implant engaging surface 234 can be milled or cut in a non-planar shape that corresponds to the posterior side 58. A passage 236 can be prepared in the ulna 232. In one example, the passage 236 can correspond with an intramedullary canal of the host ulna. It will be appreciated that the particular geometry of the surface 234 and the passage 236 is merely exemplary and the host ulna 232 may be prepared differently according to the needs of a particular patient.

Figure 5C:
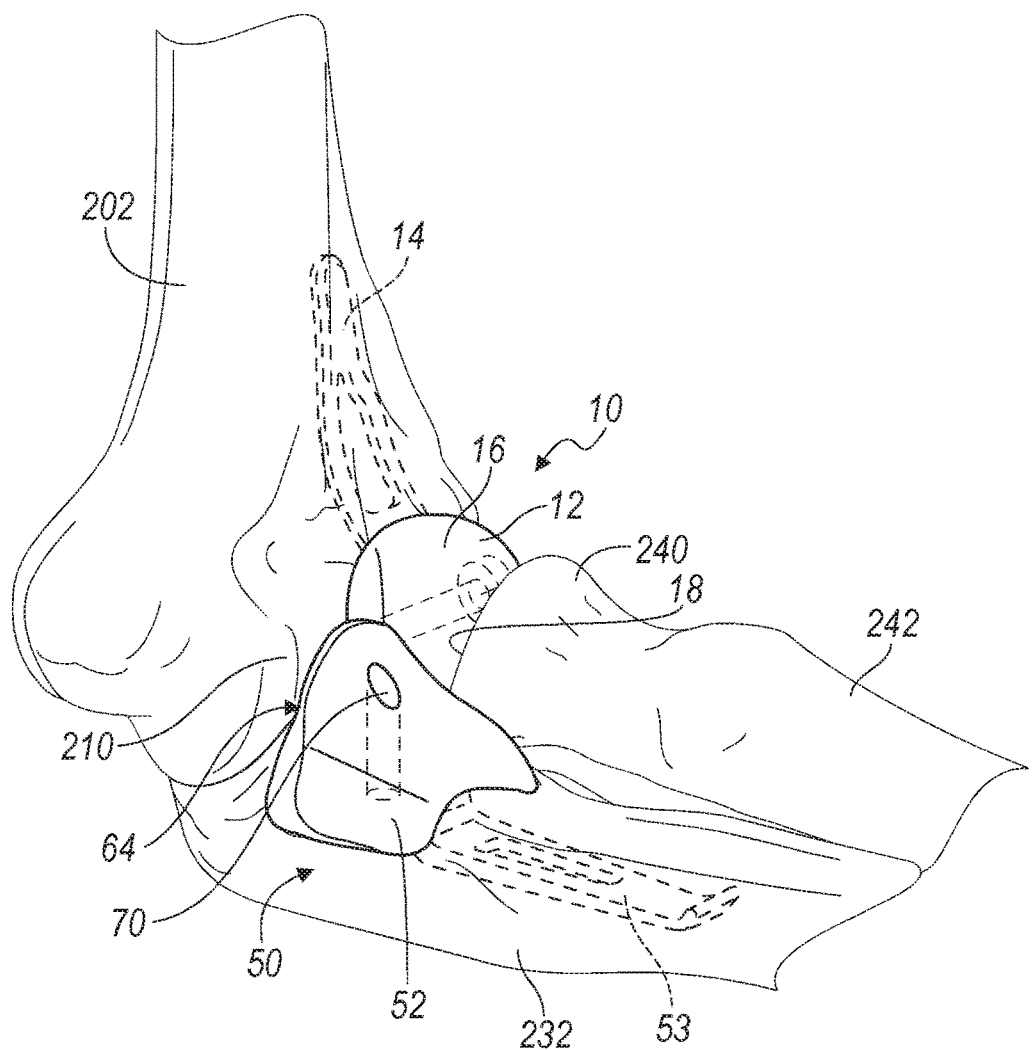
FIG. 5C is an exemplary implanted position of the capitellar and coronoid implants of FIGS. 1A-2F according to one example.
Figure 5D:
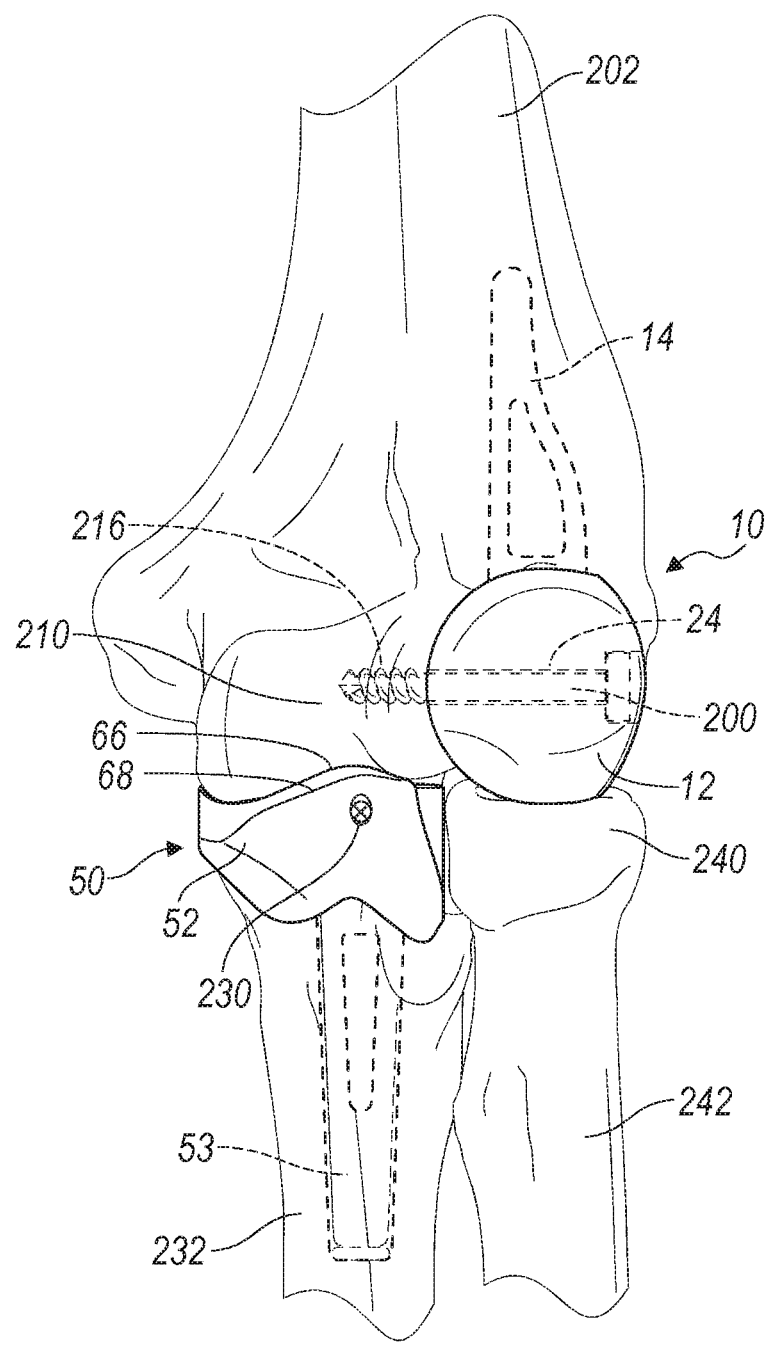
FIG. 5D is an anterior view of the implanted capitellar and coronoid implants shown in FIG. 5C.

Turning now to FIG. 5C, the capitellar implant 10 and the coronoid implant 50 are shown implanted into an exemplary left elbow. For clarity, the bone screws 200 and 230 have been omitted from the illustration in FIG. 5C. As shown, the articulating surface 18 of the articulating body 16 of the capitellar implant 10 can be aligned for articulation with a head 240 of a radius 242. The coronoid implant 50 can be positioned relative to the ulna 232, such that the superior articulating surface 64 is aligned for slidable articulation with the trochlea 210. As shown in FIG. 5C, the capitellar implant 10 and the coronoid implant 50 are illustrated in an implanted position relative to a left elbow in extension. Notably, the bone screw 200 has been passed through the passage 24 from a lateral to a medial direction, such that the threaded end 216 threadably advances into the trochlea 210. The bone screw 200 therefore can provide additional fixation of the capitellar implant 10 relative to the host humerus 202 in addition to the fixation properties provided by the stem 14. It will be appreciated that bone screws having a longer shaft (than depicted in the Figs.) may be used when it may be desired to penetrate further into the trochlear. In addition, the bone screw 230 is shown advanced through the passage 70 provided in the articulating portion 52 of the coronoid implant 50. The bone screw 230 can threadably advance into the host ulna 232 to provide supplemental fixation of the coronoid implant 50 relative to the ulna 232 in addition to the stem 53. In some examples, bone cement may also be used such as around the stem 14.

Figure 5E:
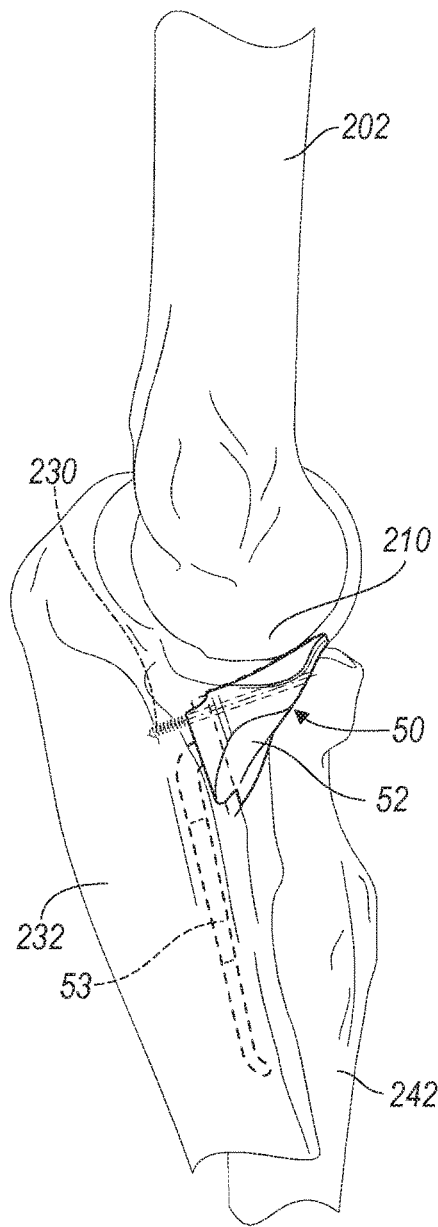
FIG. 5E is a medial view of a left elbow in extension shown with the coronoid implant of FIGS. 2A-2F implanted relative to a host ulna.
Figure 5F:
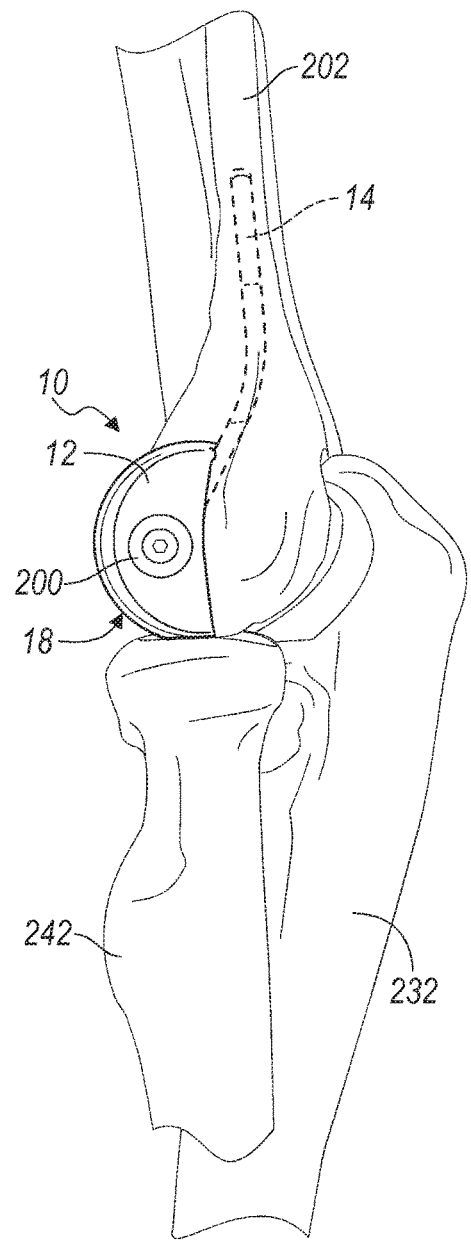
FIG. 5F is a lateral view of a left elbow in extension shown with the capitellar implant of FIGS. 1A-1E implanted relative to a distal humerus.
Figure 5G:
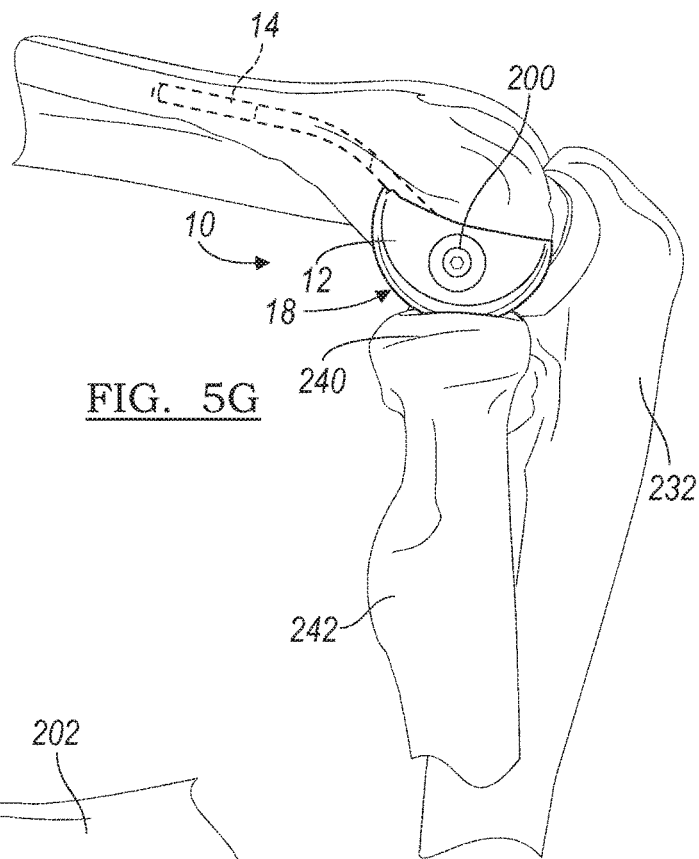
FIG. 5G is a lateral view of the capitellar implant of FIG. 5F shown with the elbow in flexion.
Figure 5H:
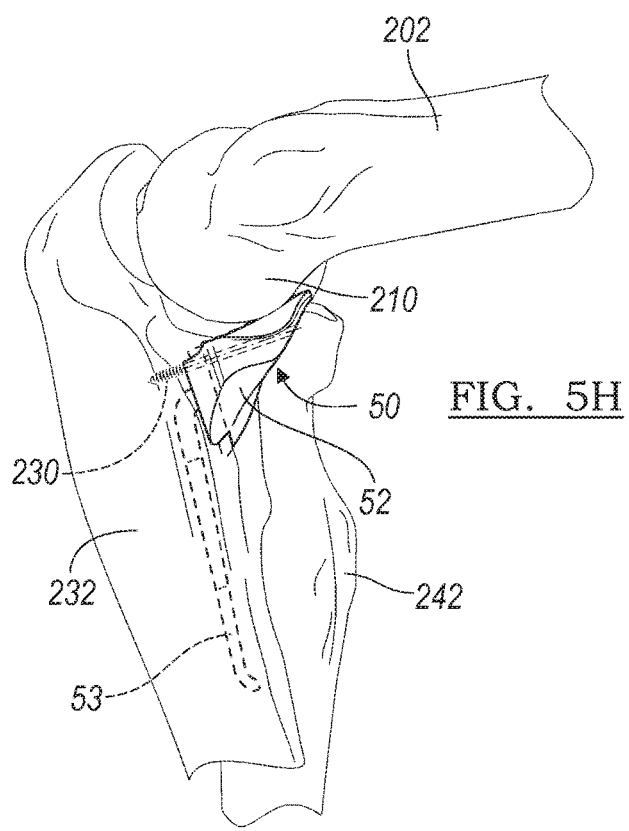
FIG. 5H is a medial view of the coronoid implant of FIGS. 2A-2F shown implanted relative to a host ulna and shown with the elbow in flexion.

The illustrations provided in FIGS. 5E-5H provide additional medial and lateral views of the capitellar and coronoid implants 10 and 50, respectively. More specifically, the coronoid implant 50 is illustrated in the medial view of the elbow joint shown with the humerus 202 and ulna 232 in extension (FIG. 5E). FIG. 5H illustrates the left elbow joint of FIG. 5E shown with the humerus 202 and the ulna 232 in flexion. As shown, the superior articulating surface 64 accommodates rotational engagement of the trochlea 210 during rotation of the humerus 202 and ulna 232. The central ridge 66 and the anterior buttress 68 on the superior articulating surface 64 of the coronoid implant 50 accommodates the geometry of the host trochlea (as best shown in FIG. 5C). The anterior buttress 68 blocks subluxation of the humerus 202 in cases of posterolateral elbow rotary instability.

With specific reference now to FIGS. 5F and 5G, the capitellar implant 10 is shown with the articulating surface 18 slidably communicating along the superior surface of the radial head 240 of the radius 242.

With reference now to FIG. 6A, the capitellar implant 110 is shown with a bone screw 200' adjacent to a humerus 202. An implant engaging surface 205 can be prepared on the distal humerus 202 subsequent to resecting at least portions of a capitellum. A passage 207 can also be prepared that can correspond with alignment to an intramedullary canal of the humerus 202. It is appreciated that the surface 205 and the passage 207 may take other forms than that shown in the example of FIG. 6A. However, it will be appreciated that the capitellar implant 110 can be implanted onto a distal humerus to accommodate coronal shear fractures involving the lateral aspect of the trochlear 210. The capitellar implant 110 can be particularly useful when it is desired to resect additional bone of the lateral trochlear (as compared to the preparation described above with respect to FIG. 5A and receipt of the capitellar implant 10). The bone screw 200' can include a head 212' and a shank 214' having a threaded end 216'. The bone screw 200' can be configured similar to the bone screw 200 described above, however, may have a longer shank 214' to extend further medially into the host trochlear 210 when implanted. In this way, the axial length of the bone screw 200' is greater than the width of the body 116 from the lateral side 130 to the medial side 132 of the articulating head 112, such that at least portions of the threaded end 216' can extend proud from the medial side 132 of the articulating head 112. In one example, the head 212' can provide a geometry substantially complementary to the counterbore 126 provided in the body 116.

Turning now to FIG. 6B, the coronoid implant 150 is shown in exploded view with a bone screw 230 and adjacent to an ulna 232. In the example shown in FIG. 6B, the ulna 232 includes an implant engaging surface 234 where a host coronoid has been resected from the ulna 232. The implant engaging surface 234 can be milled (or cut) to a shape that generally accommodates the wrap-around profile of posterior side 158. A passage 236 can be prepared in the ulna 232. In one example, the passage 236 can correspond with an intramedullary canal of the host ulna. It will be appreciated that the particular geometry of the surface 234 and the passage 236 is merely exemplary and the host ulna 232 may be prepared differently according to the needs of a particular patient.

Figure 6C:
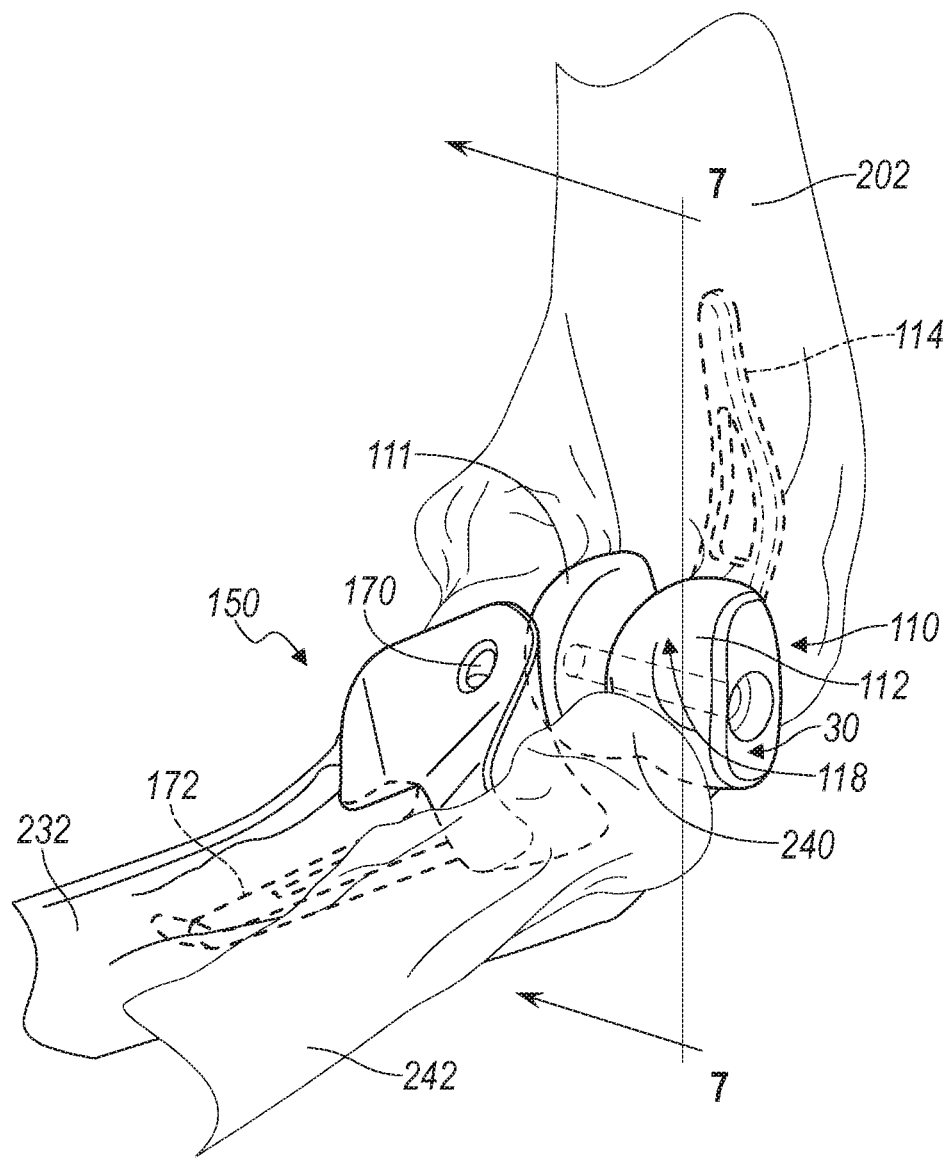
FIG. 6C is a lateral perspective view of a left elbow shown with the capitellar and coronoid implants of FIGS. 3A-4F in an implanted position relative to the host humerus and ulna, respectively, and shown with the elbow in flexion.

Turning now to FIG. 6C, the capitellar implant 112 and the coronoid implant 150 are shown implanted into an exemplary left elbow. For clarity, the bone screw 200' and 230 have been omitted from the illustration in FIG. 6C. As shown, the articulating surface 118 of the articulating body 116 of the capitellar implant 110 can be aligned for articulation with a head 240 of a radius 242. The coronoid implant 150 can be positioned relative to the ulna 232, such that the superior articulating surface 164 is aligned for slidable articulation with the trochlear 210. In the example shown, the articulating surface 164 can be configured with rotation along a portion of the host trochlear 210 and the second articulating surface 119 of the extension portion 111 on the capitellar implant 110.

Figure 6D:
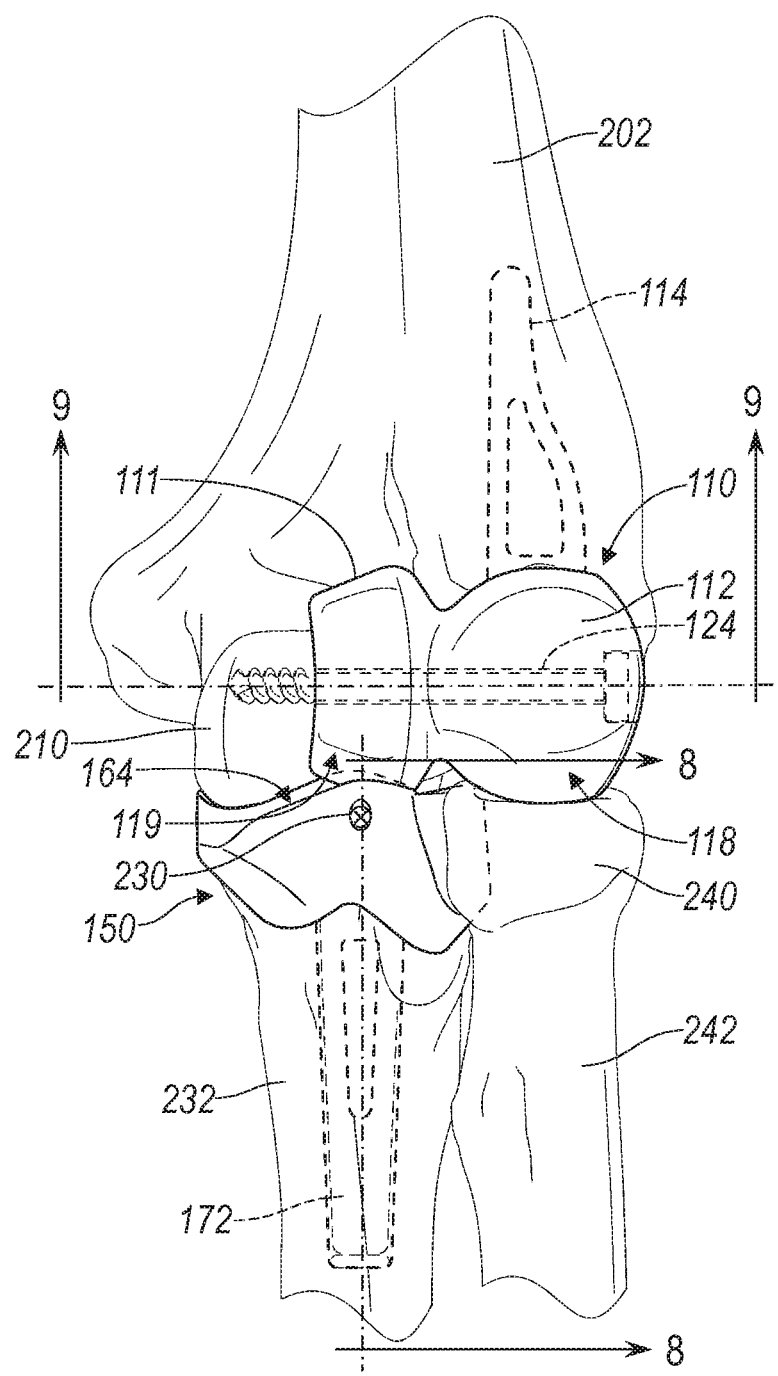
FIG. 6D is an anterior view of the capitellar and coronoid implants of FIGS. 3A-4F shown implanted into a left elbow and shown with the elbow in extension.
Figure 7:
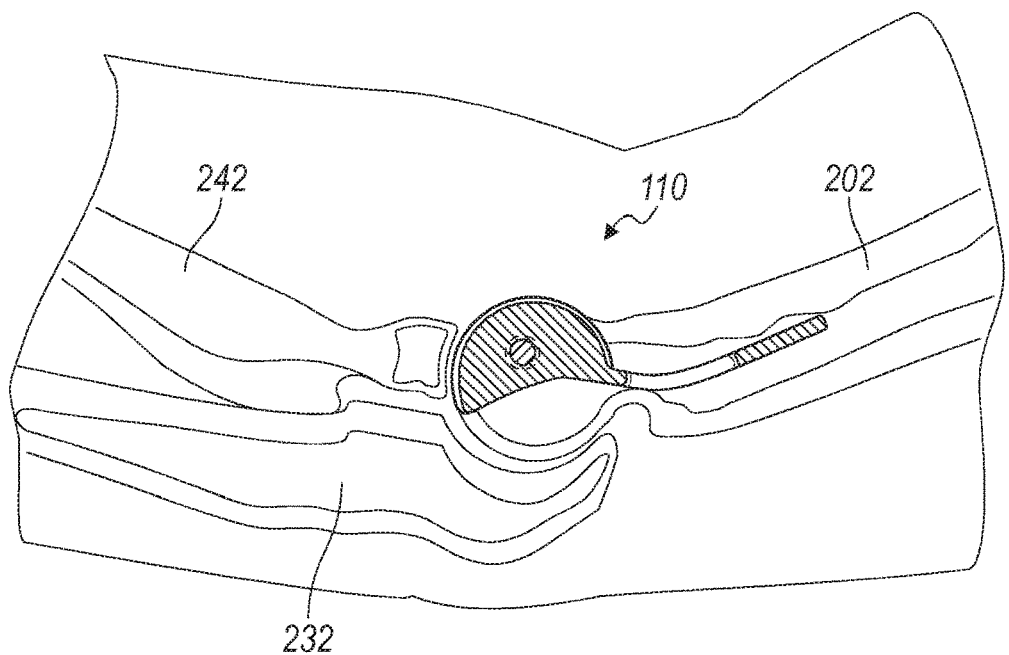
FIG. 7 is a cross-sectional view taken along lines 7-7 of FIG. 6C.
Figure 8:
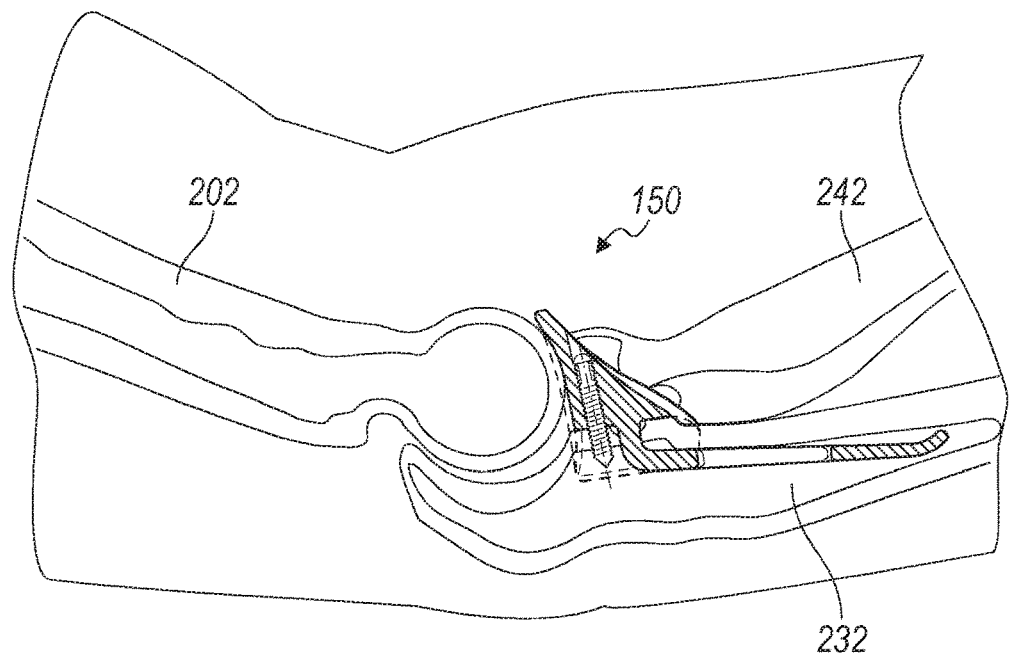
FIG. 8 is a cross-sectional view taken along lines 8-8 of FIG. 6D.
Figure 9:
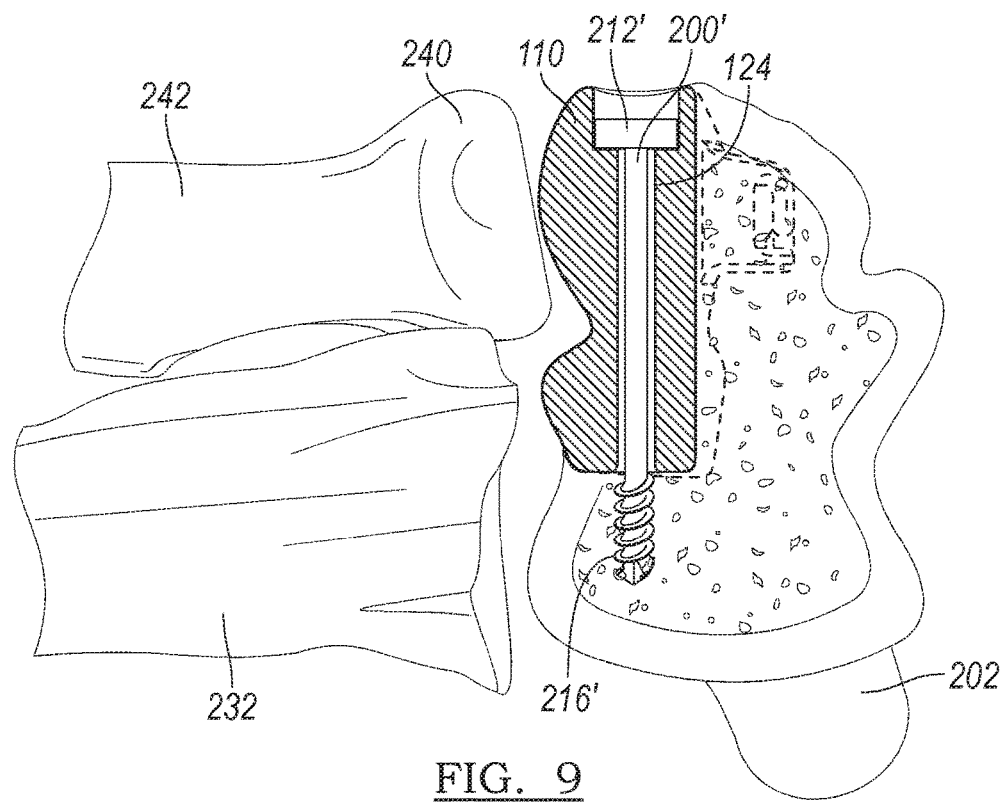
FIG. 9 is a cross-sectional view taken along lines 9-9 of FIG. 6D.
Figure 10:
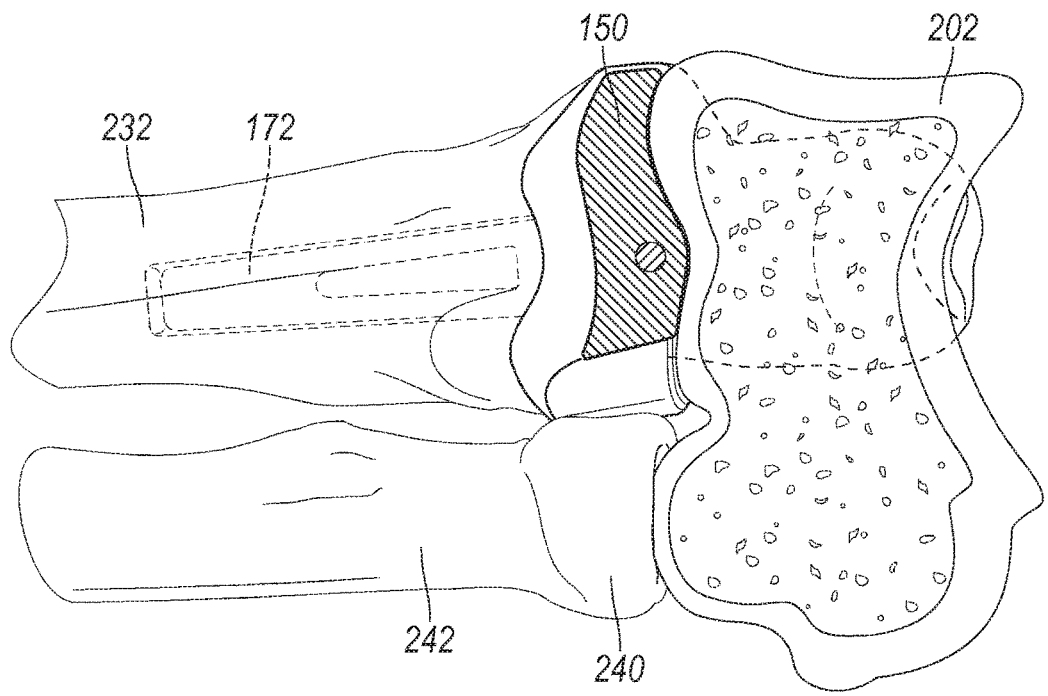
FIG. 10 is a cross-sectional view taken along lines 10-10 of FIG. 6E.

As shown in FIG. 6D, the capitellar implant 110 and the coronoid implant 150 are illustrated in an implanted position relative to a left elbow in extension. Notably, the bone screw 200' has been passed through the passage 124 from a lateral to a medial direction, such that the threaded end 216' threadably advances into the trochlear 210. The bone screw 200' therefore can provide additional fixation of the capitellar implant 110 relative to the host humerus 202 in addition to the fixation properties provided by the stem 114. Furthermore, the bone screw 230 is shown advanced through the passage 170 provided in the articulating portion 152 of the coronoid implant 150. The bone screw 230 can threadably advance into the host ulna 232 in a direction that is substantially perpendicular to a long axis of the stem 172. The bone screw 230 can provide supplemental fixation of the coronoid implant 150 relative to the ulna 232 in addition to the stem 172.

The illustrations provided in FIGS. 6E and 6F provide additional medial and lateral views of the coronoid and capitellar implants 150 and 10, respectively. More specifically, the coronoid implant 150 is illustrated in the medial view of the elbow joint shown with the humerus 202 and ulna 232 in extension (FIG. 6E). FIG. 6F shows the capitellar implant in the lateral view of the elbow joint shown with the humerus 202 and the ulna 232 in extension. The central ridge 166 and the anterior buttress 168 on the superior articulating surface 164 of the coronoid implant 150 accommodates the geometry of the host trochlear 210 (as best shown in FIG. 6D). The anterior buttress 168 blocks subluxation of the humerus 202 in cases of posterolateral elbow rotary instability. The cross-sectional views of FIGS. 7-10 provide additional views of the various capitellar and coronoid implants 110 and 150 in an implanted position.

Figure 11A:
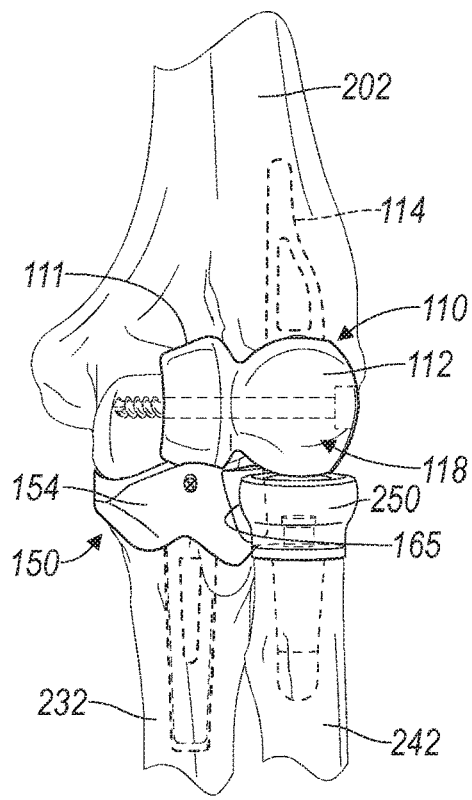
FIG. 11A is an anterior view of the capitellar and coronoid implants of FIGS. 3A-4F shown cooperating with a radial implant of a left elbow in extension.
Figure 11B:
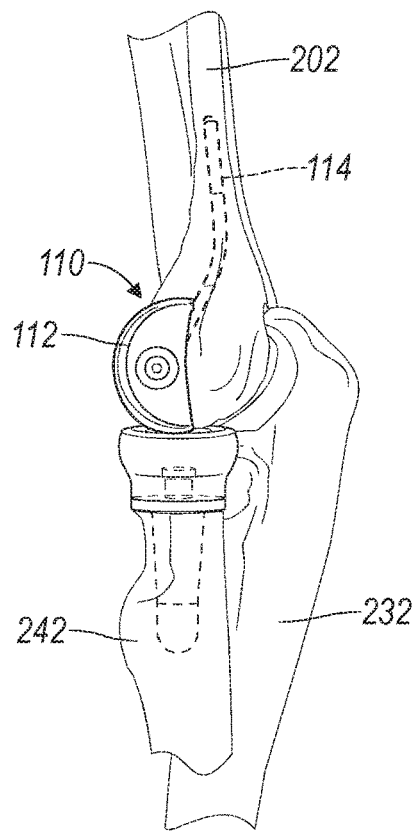
FIG. 11B is a lateral view of the capitellar and radial implants of FIG. 11A and shown with the elbow in extension.
Figure 11C:
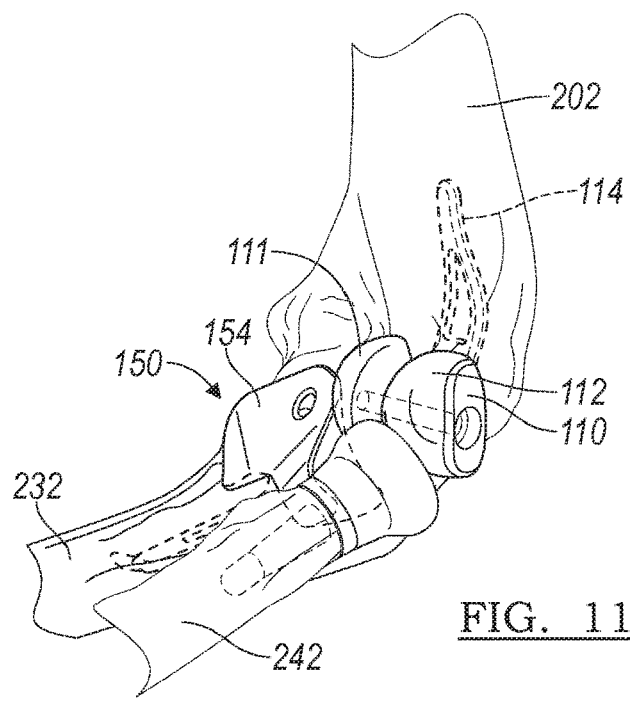
Figure 12:
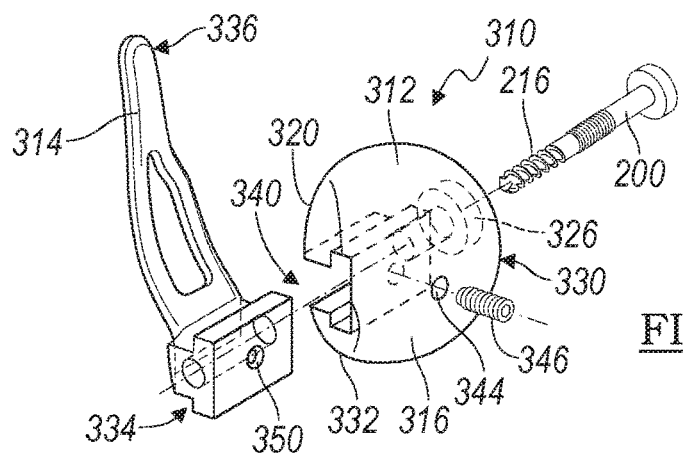
FIG. 12 is a medial perspective exploded view of a modular capitellar implant according to various features of the present teaching.
Figure 13:
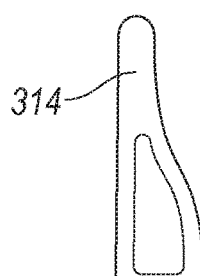
FIG. 13 is a cross-sectional view of the modular capitellar implant of FIG. 12 and taken along the axis of the fastener.
Figure 14:
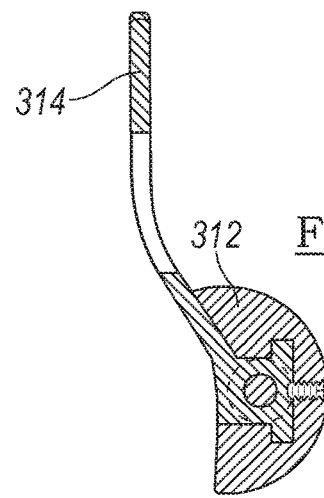
FIG. 14 is a cross-sectional view of the modular capitellar implant of FIG. 12 and taken along a plane perpendicular to an axis of the fastener.

Turning now to FIGS. 11A-11C, the capitellar implant 112 and the coronoid implant 150 are shown implanted into a host humerus 202 and ulna 232, respectively. The coronoid implant 150 is shown cooperating with an exemplary radial implant 250 that is shown implanted into the host radius 242. Additional features of the radial implant 250 can be found in commonly owned U.S. Pat. No. 6,656,225, which is expressly incorporated herein by reference. In this way, the articulating surface 118 of the articulating head 112 can slidably communicate along an opposing surface of the radial implant 250. In addition, according to some examples, the radial articulating surface 165 of the coronoid implant 150 can communicate with the radial implant 250. It will be appreciated that the radial implant 250 is merely exemplary and other radial implants may be provided for cooperating with either or both of the capitellar implant 110 and coronoid implant 150.

Figure 15:
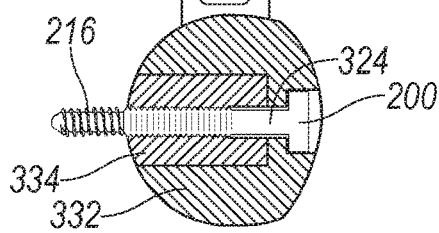
FIG. 15 is a perspective view of an exemplary kit having a plurality of modular articulating heads that each couple with a stem according to various features of the present teachings.

With reference now to FIGS. 12-15, a capitellar implant 310 constructed in accordance to additional features of the present teachings will be described. The capitellar implant 310 generally comprises a modular articulating head 312 and a stem 314. The articulating head 312 can include an articulating body 316 and a humeral engaging surface 320. A passage 324 having a counterbore 326 can be formed through the articulating body 316 from a lateral side 330 to a medial side 332. The articulating body 316 of the articulating head 312 can be modular and can be provided as part of a kit 333 (FIG. 15). As can be appreciated, a plurality of modular articulating heads (along with different size stems) 312A-312F can be provided that have various geometries, such that a surgeon can select an appropriate match based upon any given patient's particular needs.

The stem 314 can generally extend from a connecting end having a first interlocking portion 334 to a distal end 336. The articulating head 312 can include a second interlocking portion that is configured to selectively receive the first interlocking portion 334 of the stem 314. In the examples shown, the first interlocking portion is in the form of a T-shaped male insertion portion and the second interlocking portion is the form of a T-shaped female receiving portion. The articulating head 312 is configured to be slidably received onto the T-shaped male insertion portion 334 from a lateral to a medial direction. In some examples, it may be desirable to connect the articulating head 312 to the stem 314 intraoperatively, such as during trialing or when it may be desirable to change an articulating head 312 without having to disturb an already implanted stem 314. The articulating head 312 can further define an opening 344 that receives a set screw 346 for further securing the articulating head 312 to a recess 350 provided on the first interlocking portion 334. In one example, articulating head 312 can be solely secured by the lock screw 200 (FIG. 13) that threads into the T-shaped male insertion of the stem and also into the medial trochlear. In another example, the articulating head 312 can be secured solely by the set screw 346. In other examples, the articulating head 312 can be secured by a combination of both the lock screw 200 and the set screw 346.

While the examples shown illustrate the male insertion portion being formed on the stem 314 and the female receiving portion being formed on the articulating head 312, these features may be swapped. Furthermore, while the specific geometries illustrated as a T-shaped section, other geometrical configurations may be provided.

While the description in the specification and illustrated in the drawings are directed to various embodiments, it will be understood that various changes may be made and equivalents may be substituted for elements thereof without departing from the scope of the teachings and the appended claims. In addition, many modifications may be made to adapt a particular situation or material to the teachings without departing from the scope thereof. Therefore, it is intended that the teachings and claims are not be limited to any particular embodiment illustrated in the drawings and described in the specification, but that the teachings and claims can include any embodiments falling within the foregoing description and the appended claims.

What is claimed is:

1. A prosthetic elbow comprising:
a coronoid implant including a body and a stem, the body having a superior articulating surface including a central ridge that extends in an anterior/posterior direction and an anterior buttress that extends in a medial/lateral direction, the central ridge configured to accommodate articulation with a trochlea in an implanted position, and the anterior buttress configured to limit subluxation of a humerus in cases of posterolateral elbow rotary instability, wherein a passage extends through the body from an anterior to a posterior side, and wherein the stem comprises a planar body that extends from a connecting end to a distal end.

2. The prosthetic elbow of claim 1, further comprising a bone screw that extends into the passage of the body and has an end that extends proud from the body and is adapted to threadably engage a host ulna in an implanted position.

3. The prosthetic elbow of claim 2, wherein the stem defines an opening therethrough, the opening adapted to accept boney ingrowth when implanted into an intermedullary canal of an ulna.

4. The prosthetic elbow of claim 3, wherein the bone screw extends substantially perpendicular relative to a long axis of the stem.

5. The prosthetic elbow of claim 2, wherein the body further comprises an extension portion that is adapted to extend generally laterally toward a radial head of a radius in an implanted position.

6. The prosthetic elbow of claim 5, wherein the body comprises a triangular-wedge-like shape that extends between an anterior side, a posterior side, a medial side, and a lateral side, and wherein the extension portion extends from the lateral side.

7. The prosthetic elbow of claim 6, wherein, when the coronoid implant is implanted in an ulna, the extension portion articulates with a radial head of the radius.

8. The prosthetic elbow of claim 6, wherein the lateral side further comprises a first radial articulating surface positioned on the lateral side of the body.

9. The prosthetic elbow of claim 8, further comprising a radial implant adapted to be implanted into a radius, the radial implant including a second radial articulating surface configured to articulate with the first radial articulating surface of the body of the coronoid implant.

10. The prosthetic elbow of claim 2, wherein the body comprises a triangular-wedge-like shape that extends between an anterior side, a posterior side, a medial side, and a lateral side.

11. The prosthetic elbow of claim 10, wherein the posterior side comprises a non-planar profile configured to engage a bone surface of the host ulna.

12. The prosthetic elbow of claim 10, wherein the stem extends along an axis, and wherein the connecting end is attached to the posterior side of the body.

13. The prosthetic elbow of claim 12, wherein the connecting end of the stem is curved.

* * * * *